US012649728B2

(12) United States Patent
Yao et al.

(10) Patent No.: US 12,649,728 B2
(45) Date of Patent: Jun. 9, 2026

(54) PYRIMIDINE CARBOXAMIDE COMPOUND AND APPLICATION THEREOF

(71) Applicant: SHANGHAI MEIYUE BIOTECH DEVELOPMENT CO., LTD, Shanghai (CN)

(72) Inventors: Yuanshan Yao, Shanghai (CN); Guozhong Ye, Shanghai (CN); Linbo Luan, Shanghai (CN); Yongkai Chen, Shanghai (CN); Chaodong Wang, Shanghai (CN)

(73) Assignee: SHANGHAI MEIYUE BIOTECH DEVELOPMENT CO., LTD, Shanghai (CN)

( * ) Notice: Subject to any disclaimer, the term of this patent is extended or adjusted under 35 U.S.C. 154(b) by 520 days.

(21) Appl. No.: 18/028,213

(22) PCT Filed: Nov. 3, 2021

(86) PCT No.: PCT/CN2021/128344
§ 371 (c)(1),
(2) Date: Mar. 23, 2023

(87) PCT Pub. No.: WO2022/063333
PCT Pub. Date: Mar. 31, 2022

(65) Prior Publication Data

US 2024/0083873 A1 Mar. 14, 2024

(30) Foreign Application Priority Data

Sep. 25, 2020 (CN) ......................... 202011020721.0
Sep. 17, 2021 (CN) ......................... 202111095465.6

(51) Int. Cl.
*C07D 401/14* (2006.01)
*C07D 487/10* (2006.01)
*C07D 491/048* (2006.01)
*C07D 491/107* (2006.01)
*C07D 519/00* (2006.01)

(52) U.S. Cl.
CPC ......... *C07D 401/14* (2013.01); *C07D 487/10* (2013.01); *C07D 491/048* (2013.01); *C07D 491/107* (2013.01); *C07D 519/00* (2013.01)

(58) Field of Classification Search
CPC ........................... C07D 487/10; C07D 401/14; C07D 491/048; C07D 491/107; C07D 519/00
See application file for complete search history.

(56) References Cited

U.S. PATENT DOCUMENTS

2019/0315715 A1 10/2019 Casimiro-Garcia et al.
2022/0204479 A1 6/2022 Zhang et al.

FOREIGN PATENT DOCUMENTS

CN 109476645 A 3/2019
WO 2018212534 A1 11/2018
WO 2020043658 A1 3/2020
WO 2020114947 A1 6/2020
WO 2020114949 A1 6/2020
WO 2020119896 A1 6/2020
WO 2020123426 A1 6/2020
WO 2021043260 A1 3/2021

OTHER PUBLICATIONS

Feb. 14, 2025 First Examination Report issued in Indian Patent Application No. 202317020946.
Mar. 15, 2024 First Office Action issued in Eurasian Patent Application No. 202390956.
May 8, 2024 First Office Action issued in Canadian Patent Application No. 3193204.
Mar. 12, 2024 First Office Action issued in Japanese Patent Application No. 2023-518317.
Sep. 22, 2023 First Office Action issued in Australian Patent Application No. 2021350973.
Nov. 26, 2024 Extended European Search Report issued in European Patent Application No. 21871566.2.
Jan. 13, 2025 First Office Action issued in Korean Patent Application No. 10-2023-7007851.
Dec. 18, 2023 First Office Action issued in Chinese Patent Application No. 202180065825.X.
Dec. 18, 2023 Search Report issued in Chinese Patent Application No. 202180065825.X.

(Continued)

*Primary Examiner* — Rebecca L Anderson

(57) ABSTRACT

Disclosed are a pyrimidine carboxamide compound and an application thereof. Further provided are a pyrimidine carboxamide compound represented by formula (I), or a tautomer, mesomer, racemate, enantiomer, or diastereomer thereof, a mixture form thereof, or a pharmaceutically acceptable salt thereof. The compound can be used as a Vanin enzyme inhibitor, and can be used to prepare a drug for treating various diseases, including Crohn's disease, ulcerative colitis, and so on.

I

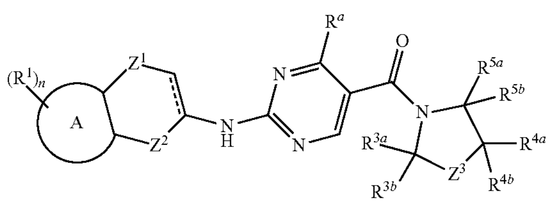

19 Claims, No Drawings

(56) References Cited

OTHER PUBLICATIONS

Feb. 10, 2022 International Search Report issued in International Patent Application No. PCT/CN2021/128344.
Feb. 10, 2022 Written Opinion of the International Searching Authority issued in International Patent Application No. PCT/CN2021/128344.
Berruyer C. et al., Vanin-1-/-mice exhibit a glutathione-mediated tissue resistance to oxidative stress, Mol. Cell Biol., Aug. 2004, pp. 7214-7224, vol. 24 (16).
Berruyer C. et al., Vanin-1 licenses inflammatory mediator production by gut epithelial cells and controls colitis by antagonizing peroxisome proliferator-activated receptor γ activity, J. Exp. Med., Dec. 25, 2006, pp. 2817-2827, vol. 203 (13).
Rommelaere S. et al., PPARalpha regulates the production of serum Vanin-1 by liver, FEBS Lett., Nov. 15, 2013, pp. 3742-3748, vol. 587 (22).
Thomas N. Sorrell, Organic Chemistry, University Science Books, Sausalito, 1999.
Michael B. Smith et al., March's Advanced Organic Chemistry, New Jersey, 2007.

PYRIMIDINE CARBOXAMIDE COMPOUND AND APPLICATION THEREOF

The present application claims priorities to Chinese Patent Application 2020110207210 filed on Sep. 25, 2020 and Chinese Patent Application 2021110954656 filed on Sep. 17, 2021. The contents of the Chinese Patent Applications are incorporated herein by reference in their entireties.

TECHNICAL FIELD

The present disclosure relates to a pyrimidine carboxamide compound and a use thereof.

BACKGROUND

Vanin-1 (vascular non-inflammatory molecule-1) is an exonuclease with pantetheinase activity, which mainly catalyzes the hydrolysis of pantetheine to produce pantothenic acid (VB5) and mercaptoethylamine. Coenzyme A (CoA), synthesized from VB5, regulates biotransformations such as fatty acid synthesis and oxidation as well as energy metabolism, while the reversible reaction between mercaptoethylamine and cystamine is an important sensor of oxidative stress. A growing number of studies have found that deficiency or reduced levels of mercaptoethylamine lead to enhanced γ-GCS activity, causing elevated endogenous GSH reserves in tissues, which may thereby prevent or eliminate tissue inflammation. Studies have found that mRNA of Vanin-1 is highly expressed in human colon, duodenum, endometrium, liver, kidney, gallbladder and small intestine. In patients with UC (ulcerative colitis), Vanin-1 was highly expressed and diffuse, and limited to brush borders. In addition, the expression level of Vanin-1 in the colon was still significantly higher than that of the control group during the clinically quiescent phase of UC. In the TNBS model experiment, the survival rate of Vanin-1 knockout (Vanin-$1^{-/-}$) mice was significantly higher than that of the model control group, and there was no significant weight loss. Moreover, 90% of Vanin-$1^{-/-}$ mice treated with cystamine died within 5 days, indicating that cystamine completely reversed the protective effect of Vanin-1 deficiency on colitis. In addition, histopathological analysis of mice has found that the inhibition or knockout of Vanin-1 can significantly ameliorate the colon lesions in mice (Berruyer C, et al. Vanin-$1^{-/-}$ mice exhibit a glutathione mediated tissue resistance to oxidative stress. Mol. Cell Biol. 2004; 24: 7214-7224; Berruyer C, et al. Vanin-1 licenses inflammatory mediator production by gut epithelial cells and controls colitis by antagonizing peroxisome proliferator-activated receptor γ activity. J. Exp. Med. 2006; 203: 2817-2827).

Furthermore, Vanin-1 is also considered to play a regulatory role in cardiovascular diseases and tumor diseases. Studies have demonstrated that Vanin-1 regulates the activation of smooth muscle cells in vitro and the development of neointimal hyperplasia in response to carotid artery ligation in vivo. VNN1 gene polymorphisms are associated with blood pressure and HDL levels. In SF-1 transgenic mice, Vanin-1 deficiency prevented the mice from developing neoplasia of the adrenal cortex, suggesting a role for Vanin-1 in certain cancers. Studies in inflammatory diseases have found that Vanin-1 is highly upregulated in psoriatic skin lesions compared to normal individuals. Gene expression of VNN1 was also upregulated in whole blood from patients with childhood immune thrombocytopenia (ITP), wherein overexpression of VNN1 was associated with the progression of chronic ITP. In addition, elevated Vanin-1 has been detected in the urine of patients with a variety of renal disorders, including systemic lupus erythematosus, nephrotoxicant-induced renal injury and type 2 diabetes (Rommelaere S, et al. PPARalpha regulates the production of serum Vanin-1 by liver. FEBS Lett. 2013 Nov. 15; 587(22): 3742-8).

SUMMARY

The technical problem to be solved by the present disclosure is to overcome the lack of Vanin enzyme-based therapeutic agents in the prior art; and provided are a pyrimidine carboxamide compound and a use thereof. The pyrimidine carboxamide compound provided by the present disclosure is a compound with Vanin enzyme inhibitory activity; it has strong Vanin-1 inhibitory activity; and it can be used to treat various diseases, comprising Crohn's disease and ulcerative colitis.

The present disclosure solves the above technical problem by the following technical solutions.

The present disclosure provides a pyrimidine carboxamide compound represented by formula I, or a tautomer, mesomer, racemate, enantiomer, diastereomer thereof, or a mixture form thereof, or a pharmaceutically acceptable salt thereof;

I

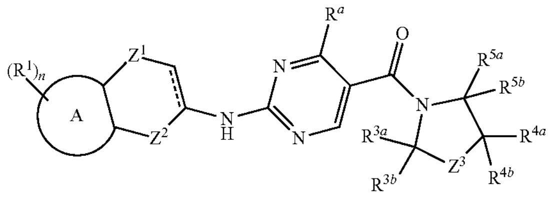

wherein, n is 0, 1, 2 or 3;

- $R^1$ is independently halogen, $C_1$-$C_6$ alkyl, $C_1$-$C_6$ alkyl substituted by one or more than one $R^{1a}$;
- $Z^1$ is —($CR^{6a}R^{6b}$)— or —($NR^{6c}$)—, and $Z^2$ is a linking bond; or, $Z^1$ is a linking bond, and $Z^2$ is —($CR^{7a}R^{7b}$)—;
- $Z^3$ is a linking bond or —($CR^{8a}R^{8b}$)—;
- $R^a$ is independently H;
- $R^{6a}$, $R^{6b}$, $R^{7a}$ and $R^{7b}$ are independently H, halogen or $C_1$-$C_6$ alkyl;
- $R^{6a}$ is independently H or $C_1$-$C_4$ alkyl;
- $R^{3a}$, $R^{3b}$, $R^{4a}$, $R^{4b}$, $R^{5a}$, $R^{5b}$, $R^{8a}$ and $R^{8b}$ are independently H, halogen, $C_1$-$C_6$ alkyl, $C_1$-$C_6$ alkyl substituted by one or more than one $R^{1c}$, —($NR^{9a}R^{9b}$) or —($NR^{10a}$)—(C═O)—$R^{10b}$;
- alternatively, $R^{4a}$ and $R^{4b}$, or, $R^{4a}$ and $R^{5a}$, or, $R^{4a}$ and $R^{8a}$ form a ring B together with the carbon to which they are bonded; the ring B is 4- to 7-membered cycloalkyl, 4- to 7-membered heterocycloalkyl, 4- to 7-membered cycloalkyl substituted by one or more than one $R^{1d}$, or 4- to 7-membered heterocycloalkyl substituted by one or more than one $R^{1e}$; the heteroatom of the 4- to 7-membered heterocycloalkyl and the 4- to 7-membered heterocycloalkyl substituted by one or more than one $R^{1e}$ is N, O or S, and the number of heteroatom is 1 or 2;
- $R^{1a}$, $R^{1c}$, $R^{1d}$ and $R^{1e}$ are independently halogen, $C_1$-$C_4$ alkyl or $C_1$-$C_4$ alkyl substituted by one or more than one halogen;

$R^{9a}$, $R^{9b}$, $R^{10a}$ and $R^{10b}$ are independently H, $C_1$-$C_4$ alkyl or $C_1$-$C_4$ alkyl substituted by one or more than one halogen;

A is phenyl or 6-membered heteroaryl; the heteroatom of the 6-membered heteroaryl is N, and the number of heteroatom is 1 or 2;

$---$ represents a single bond or a double bond.

In some preferred embodiments of the present disclosure, some groups of the pyrimidine carboxamide compound represented by formula I, or the tautomer, mesomer, racemate, enantiomer, diastereomer thereof, or the mixture form thereof, or the pharmaceutically acceptable salt thereof are defined as follows, and unmentioned groups are the same as those described in any one of the embodiments in the present disclosure (hereinafter referred to as "in a certain embodiment"), n is 0 or 1.

In a certain embodiment, $Z^1$ is —($CR^{6a}R^{6b}$)—, and $Z^2$ is the linking bond.

In a certain embodiment, $R^{6a}$ and $R^{6b}$ are independently H or halogen.

In a certain embodiment, $R^{7a}$ and $R^{7b}$ are independently H; that is, $Z^2$ is —($CH_2$)—.

In a certain embodiment, $Z^3$ is —($CR^{8a}R^{8b}$)—.

In a certain embodiment, $R^{3a}$, $R^{3b}$, $R^{4a}$, $R^{4b}$, $R^{5a}$, $R^{5b}$, $R^{8a}$ and $R^{8b}$ are independently H, $C_1$-$C_6$ alkyl, —($NR^{9a}R^{9b}$) or —($NR^{10a}$)—(C═O)—$R^{10b}$.

In a certain embodiment, $R^{3a}$ and $R^{3b}$ are independently H.

In a certain embodiment, $R^{5a}$ and $R^{5b}$ are independently H.

In a certain embodiment, $R^{4a}$ and $R^{4b}$ are independently H, $C_1$-$C_6$ alkyl, —($NR^{9a}R^{9b}$) or —($NR^{10a}$)—(C═O)—$R^{10b}$.

In a certain embodiment, $R^{4a}$ is independently $C_1$-$C_6$ alkyl, —($NR^{9a}R^{9b}$) or —($NR^{10a}$)—(C═O)—$R^{10b}$;

$R^{4b}$ is independently H or $C_1$-$C_6$ alkyl.

In a certain embodiment, $R^{4a}$ and $R^{4b}$, or, $R^{4a}$ and $R^{5a}$, or, $R^{4a}$ and $R^{8a}$ form the ring B together with the carbon to which they are bonded;

for example, the ring B is 4- to 7-membered cycloalkyl, 4- to 7-membered heterocycloalkyl, 4- to 7-membered heterocycloalkyl substituted by one or more than one $R^{1d}$.

In a certain embodiment, $R^{8a}$ and $R^{8b}$ are independently H; that is, $Z^3$ is —($CH_2$)—.

In a certain embodiment, $R^{1a}$, $R^{1c}$, $R^{1d}$ and $R^{1e}$ are independently halogen or $C_1$-$C_4$ alkyl.

In a certain embodiment, $R^{1a}$ is independently halogen; for example, F.

In a certain embodiment, $R^{1e}$ is independently $C_1$-$C_4$ alkyl.

In a certain embodiment, $R^{9a}$, $R^{9b}$, $R^{10a}$ and $R^{10b}$ are independently $C_1$-$C_4$ alkyl or $C_1$-$C_4$ alkyl substituted by one or more than one halogen.

In a certain embodiment,

A is 6-membered heteroaryl; for example, pyridyl.

In a certain embodiment, $---$ represents the single bond.

In a certain embodiment,

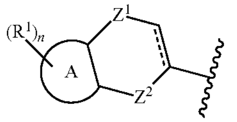

is

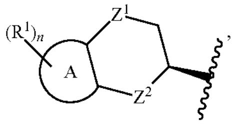

,

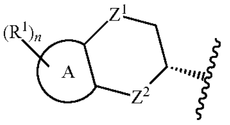

or a mixture thereof; for example,

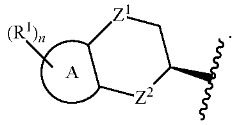

.

In a certain embodiment, n is 0 or 1;

$R^1$ is independently halogen, $C_1$-$C_6$ alkyl, $C_1$-$C_6$ alkyl substituted by one or more than one $R^{1a}$;

$Z^1$ is —($CR^{6a}R^{6b}$)— or —($NR^{6c}$)—, and $Z^2$ is the linking bond; or, $Z^1$ is the linking bond, and $Z^2$ is —($CR^{7a}R^{7b}$)—;

$Z^3$ is —($CR^{8a}R^{8b}$)—;

$R^a$ is independently H;

$R^{6a}$, $R^{6b}$, $R^{7a}$ and $R^{7b}$ are independently H or halogen;

$R^{6c}$ is independently H or $C_1$-$C_4$ alkyl;

$R^{3a}$, $R^{3b}$, $R^{5a}$, $R^{5b}$, $R^{8a}$ and $R^{8b}$ are independently H;

$R^{4a}$ and $R^{4b}$ are independently H, $C_1$-$C_6$ alkyl, —($NR^{9a}R^{9b}$) or —($NR^{10a}$)—(C═O)—$R^{10b}$;

alternatively, $R^{4a}$ and $R^{4b}$, or, $R^{4a}$ and $R^{5a}$, or, $R^{4a}$ and $R^{8a}$ form the ring B together with the carbon to which they are bonded; the ring B is 4- to 7-membered cycloalkyl, 4- to 7-membered heterocycloalkyl, 4- to 7-membered cycloalkyl substituted by one or more than one $R^{1d}$, or 4- to 7-membered heterocycloalkyl substituted by one or more than one $R^{1e}$;

$R^{1a}$, $R^{1d}$ and $R^{1e}$ are independently halogen or $C_1$-$C_4$ alkyl;

$R^{9a}$, $R^{9b}$, $R^{10a}$ and $R^{10b}$ are independently $C_1$-$C_4$ alkyl or $C_1$-$C_4$ alkyl substituted by one or more than one halogen;

A is phenyl or 6-membered heteroaryl;

$---$ represents the single bond or the double bond.

In a certain embodiment, n is 0 or 1;

$R^1$ is independently halogen, $C_1$-$C_6$ alkyl, $C_1$-$C_6$ alkyl substituted by one or more than one $R^{1a}$;

$Z^1$ is —($CR^{6a}R^{6b}$)— or —($NR^{6c}$)—, and $Z^2$ is the linking bond; or, $Z^1$ is the linking bond, and $Z^2$ is —($CR^{7a}R^{7b}$)—;

$Z^3$ is —($CR^{8a}R^{8b}$)—;

$R^a$ is independently H;

$R^{6a}$ and $R^{6b}$ are independently H or halogen; lea and $R^{7b}$ are independently H;

$R^{1a}$ is independently halogen;

$R^{6c}$ is independently H or $C_1$-$C_4$ alkyl;

$R^{3a}$, $R^{3b}$, $R^{5a}$, $R^{5b}$, $R^{8a}$ and $R^{8b}$ are independently H;

$R^{4a}$ is independently $C_1$-$C_6$ alkyl, —($NR^{9a}R^{9b}$) or —($NR^{10a}$)—(C═O)—$R^{10b}$;

$R^{4b}$ is independently H or $C_1$-$C_6$ alkyl;

alternatively, $R^{4a}$ and $R^{4b}$, or, $R^{4a}$ and $R^{5a}$, or, $R^{4a}$ and $R^{8a}$ form the ring B together with the carbon to which they are bonded; the ring B is 4- to 7-membered cycloalkyl, 4- to 7-membered heterocycloalkyl, or 4- to 7-membered heterocycloalkyl substituted by one or more than one $R^{1e}$;

$R^{1e}$ is independently $C_1$-$C_4$ alkyl;

$R^{9a}$, $R^{9b}$, $R^{10a}$ and $R^{10b}$ are independently $C_1$-$C_4$ alkyl or $C_1$-$C_4$ alkyl substituted by one or more than one halogen;

A is 6-membered heteroaryl; for example, pyridyl;

$---$ represents the single bond.

In a certain embodiment, when $R^1$ is halogen, the halogen is fluorine, chlorine or bromine; for example, fluorine or chlorine; for another example, fluorine.

In a certain embodiment, when $R^1$ is $C_1$-$C_6$ alkyl substituted by one or more than one $R^{1a}$, the number of the substituent is 1, 2, 3, 4 or 5; for example, 1, 2 or 3; for example, trifluoromethyl.

In a certain embodiment, when $R^1$ is $C_1$-$C_6$ alkyl or $C_1$-$C_6$ alkyl substituted by one or more than one $R^{1a}$, the $C_1$-$C_6$ alkyl (such as methyl, ethyl, propyl, butyl, pentyl or hexyl) is independently $C_1$-$C_4$ alkyl (such as methyl, ethyl, n-propyl, isopropyl, n-butyl, isobutyl, sec-butyl or tert-butyl); for example, methyl.

In a certain embodiment, when $R^{6a}$, $R^{6b}$, $R^{7a}$ and $R^{7b}$ are independently halogen, the halogen is independently fluorine, chlorine or bromine; for example, fluorine or chlorine; for another example, fluorine.

In a certain embodiment, when $R^{6a}$, $R^{6b}$, $R^{7a}$ and $R^{7b}$ are independently $C_1$-$C_6$ alkyl, the $C_1$-$C_6$ alkyl (such as methyl, ethyl, propyl, butyl, pentyl or hexyl) is independently $C_1$-$C_4$ alkyl (such as methyl, ethyl, n-propyl, isopropyl, n-butyl, isobutyl, sec-butyl or tert-butyl); for example, methyl.

In a certain embodiment, when $R^{6c}$ is independently $C_1$-$C_4$ alkyl, the $C_1$-$C_4$ alkyl is methyl, ethyl, n-propyl, isopropyl, n-butyl, isobutyl, sec-butyl or tert-butyl; for example, methyl.

In a certain embodiment, when $R^{3a}$, $R^{3b}$, $R^{4a}$, $R^{4b}$, $R^{5a}$, $R^{5b}$, $R^{8a}$ and $R^{8b}$ are independently halogen, the halogen is independently fluorine, chlorine or bromine; for example, fluorine or chlorine; for another example, fluorine.

In a certain embodiment, when $R^{3a}$, $R^{3b}$, $R^{4a}$, $R^{4b}$, $R^{5a}$, $R^{5b}$, $R^{8a}$ and $R^{8b}$ are independently $C_1$-$C_6$ alkyl or $C_1$-$C_6$ alkyl substituted by one or more than one $R^{1c}$, the $C_1$-$C_6$ alkyl (such as methyl, ethyl, propyl, butyl, pentyl or hexyl) is independently $C_1$-$C_4$ alkyl (such as methyl, ethyl, n-propyl, isopropyl, n-butyl, isobutyl, sec-butyl or tert-butyl); for example, methyl or ethyl.

In a certain embodiment, when ring B is 4- to 7-membered cycloalkyl or 4- to 7-membered cycloalkyl substituted by one or more than one $R^{1d}$, the 4- to 7-membered cycloalkyl is independently cyclobutyl, cyclopentyl, cyclohexyl or cycloheptyl; for another example, cyclopentyl.

In a certain embodiment, when the ring B is 4- to 7-membered heterocycloalkyl or 4- to 7-membered heterocycloalkyl substituted by one or more than one $R^{1e}$, the 4- to 7-membered heterocycloalkyl is independently tetrahydrofuranyl, tetrahydro-2H-pyranyl, pyrrolidinyl; for example, when $R^{4a}$ and $R^{4b}$ form the ring B together with the carbon to which they are bonded, the ring B is

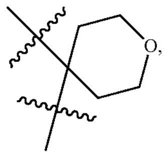

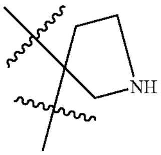

,

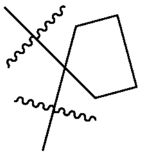

or

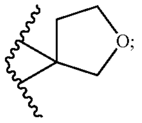

when $R^{4a}$ and $R^{5a}$, or, $R^{4a}$ and $R^{8a}$ form the ring B together with the carbon to which they are bonded, the ring B is

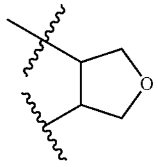

or

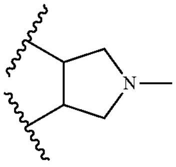

In a certain embodiment, when $R^{1a}$, $R^{1c}$, $R^{1d}$ and $R^{1e}$ are independently halogen or $C_1$-$C_4$ alkyl substituted by one or more than one halogen, the halogen is independently fluorine, chlorine or bromine; for example, fluorine or chlorine; for another example, fluorine.

In a certain embodiment, when $R^{1a}$, $R^{1c}$, $R^{1d}$ and $R^{1e}$ are independently $C_1$-$C_4$ alkyl or $C_1$-$C_4$ alkyl substituted by one or more than one halogen, the $C_1$-$C_4$ alkyl is independently methyl, ethyl, n-propyl, isopropyl, n-butyl, isobutyl, sec-butyl or tert-butyl; for example, methyl or ethyl.

In a certain embodiment, when $R^{9a}$, $R^{9b}$, $R^{10a}$ and $R^{10b}$ are independently $C_1$-$C_4$ alkyl, the $C_1$-$C_4$ alkyl is independently methyl, ethyl, n-propyl, isopropyl, n-butyl, isobutyl, sec-butyl or tert-butyl; for example, methyl or ethyl.

In a certain embodiment, when $R^{9a}$, $R^{9b}$, $R^{10a}$ and $R^{10b}$ are independently $C_1$-$C_4$ alkyl substituted by one or more than one halogen, the $C_1$-$C_4$ alkyl is independently methyl, ethyl, n-propyl, isopropyl, n-butyl, isobutyl, sec-butyl or tert-butyl; for example, methyl or ethyl.

In a certain embodiment, when $R^{9a}$, $R^{9b}$, $R^{10a}$ and $R^{10b}$ are independently $C_1$-$C_4$ alkyl substituted by one or more than one halogen, the halogen is independently fluorine, chlorine or bromine; for example, fluorine; for another example, the $C_1$-$C_4$ alkyl substituted by one or more than one halogen is trifluoromethyl.

In a certain embodiment, when A is 6-membered heteroaryl, the 6-membered heteroaryl is pyridyl, pyrazinyl or pyrimidinyl; the pyridyl may be

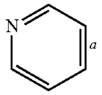

or

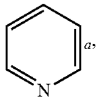

the pyrazinyl may be

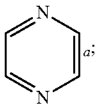

the pyrimidinyl may be

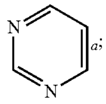

a refers to a common bond between A and

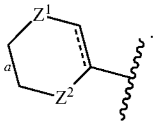

In a certain embodiment, $R^1$ is independently F, methyl or trifluoromethyl.

In a certain embodiment, $Z^1$ is —($CH_2$)—, —($CF_2$)—, —(NH)— or —(N($CH_3$))—.

In a certain embodiment, $R^{4a}$ and $R^{4b}$ are independently H, ethyl, dimethylamino,

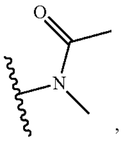

,

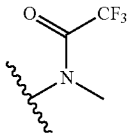

or

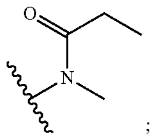

;

for example, $R^{4a}$ and $R^{4b}$ are independently ethyl, or $R^{4a}$ is H, and $R^{4b}$ is dimethylamino,

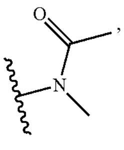

,

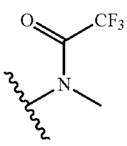

or

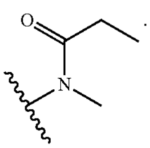

.

In a certain embodiment, $R^{4a}$ and $R^{4b}$ form the ring B together with the carbon to which they are bonded; for example,

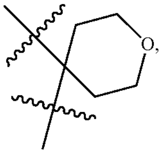

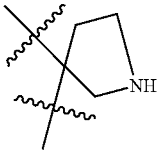

,

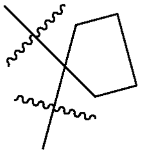

or

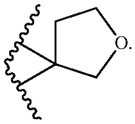

In a certain embodiment, $R^{4a}$ and $R^{5a}$, or, $R^{4a}$ and $R^{8a}$ form the ring B together with the carbon to which they are bonded; for example,

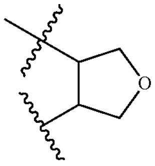

or

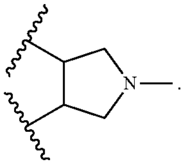

In a certain embodiment,

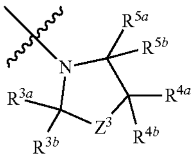

is

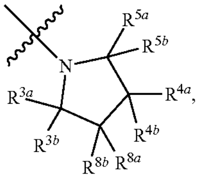

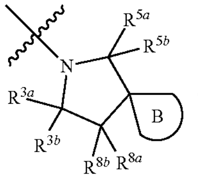

or

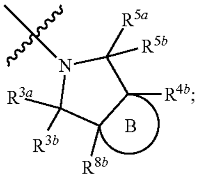

for example,

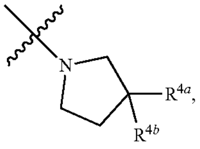

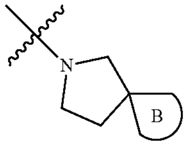

or

-continued
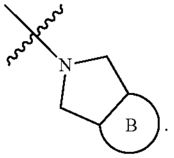
In a certain embodiment,
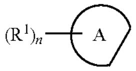
is phenyl,
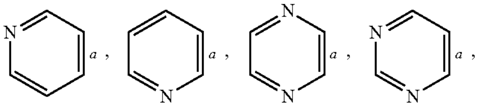
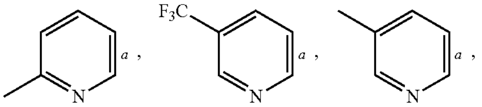
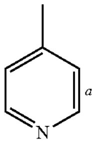 or 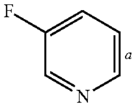 ;
for example,
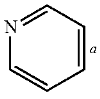 or 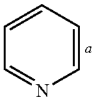 .
("a" represents the position of fusion)
In a certain embodiment,
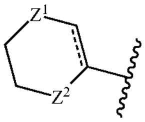 is
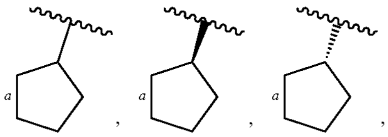
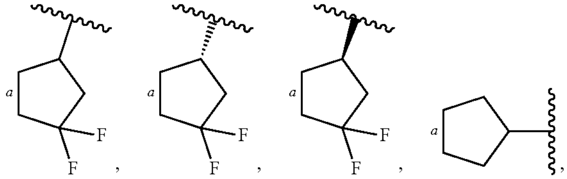
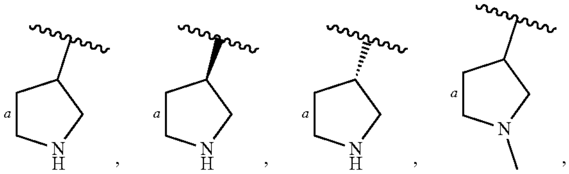
-continued
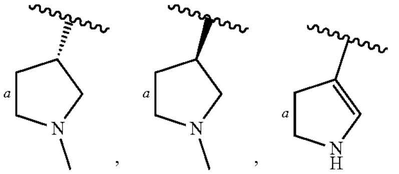 or 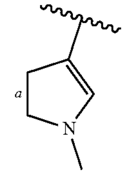 ;
for example,
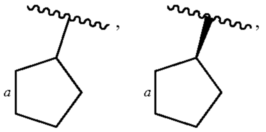 or 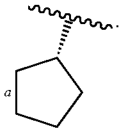 .
In a certain embodiment,
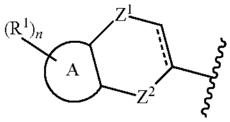
is
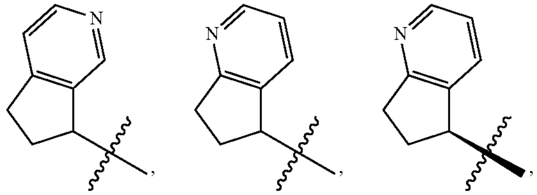
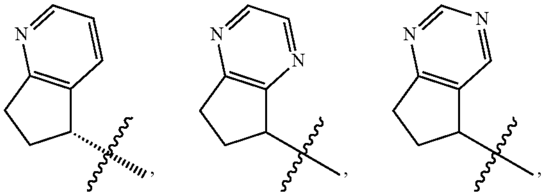
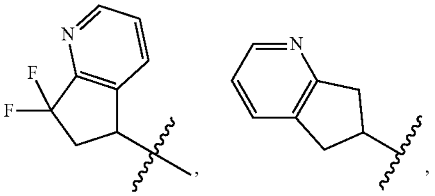
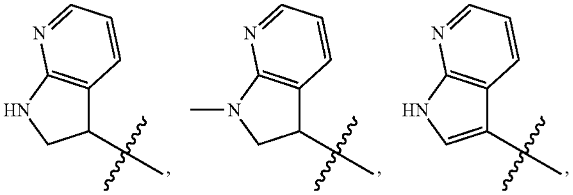

-continued
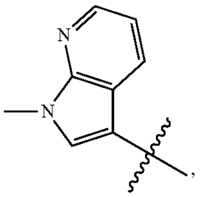,
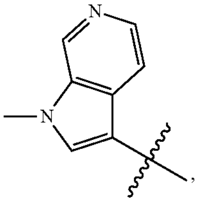,
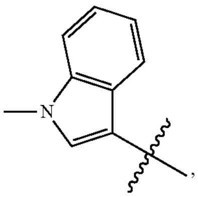,
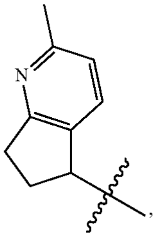,
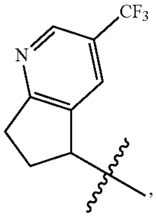,
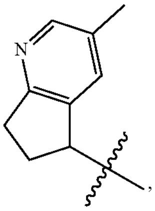,
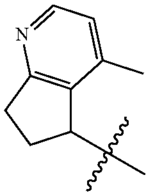 or
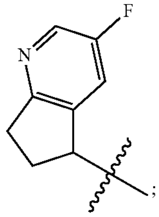;
for example,
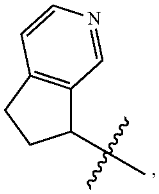,
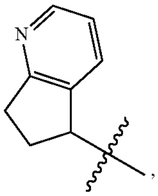,
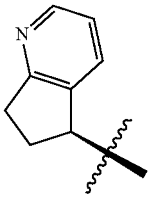 or
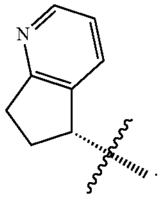.
In a certain embodiment,
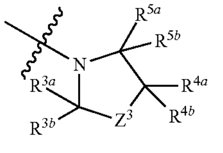
is
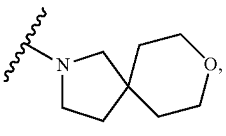
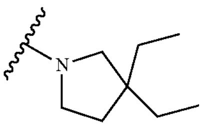,
-continued
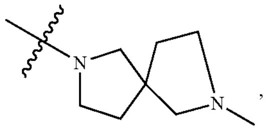,
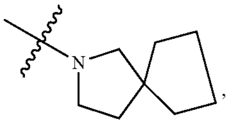,
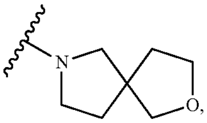
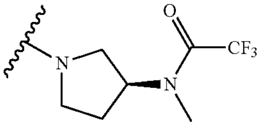,
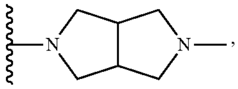
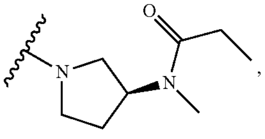,
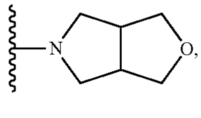
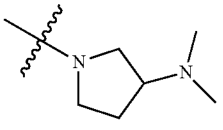 or
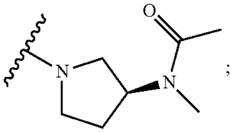;
for example,
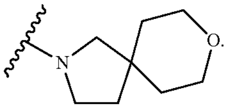 [SMILES: *N1CCC2(CCOCC2)C1]
In some preferred embodiments of the present disclosure, the pyrimidine carboxamide compound represented by formula I is any one of the following structures:
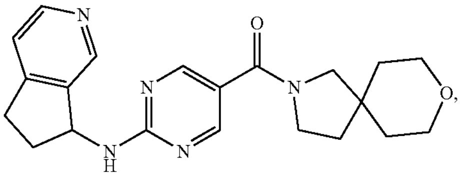
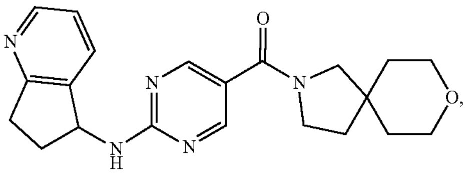
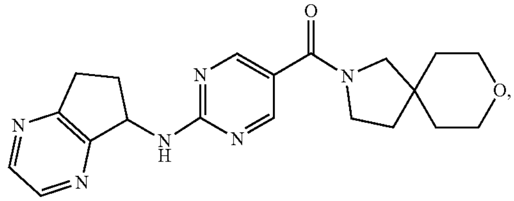

-continued
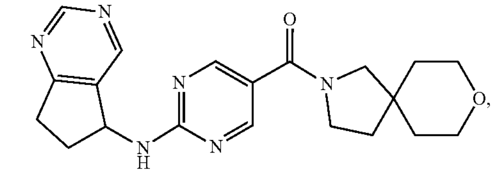
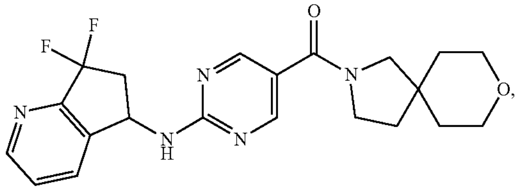
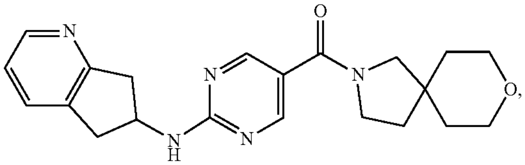
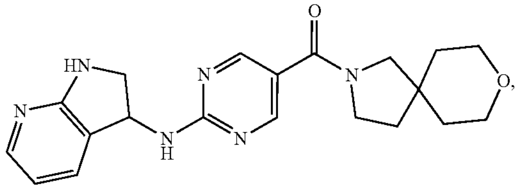
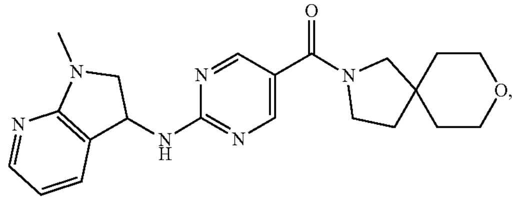
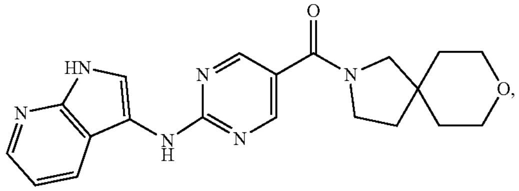
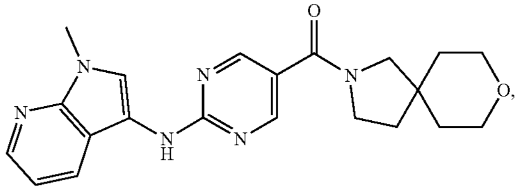
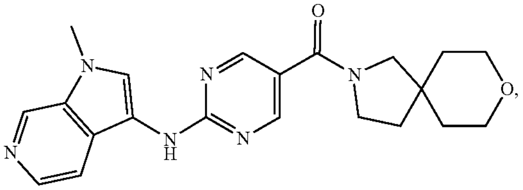
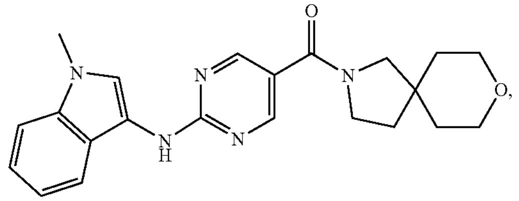
-continued
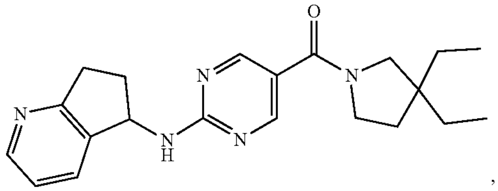
,
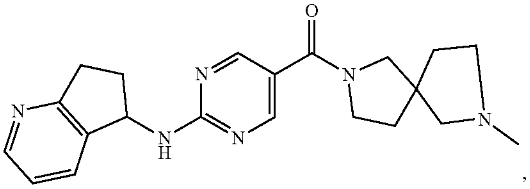
,
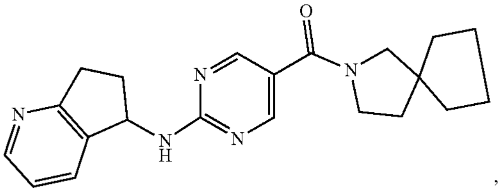
,
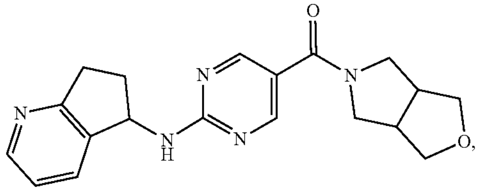
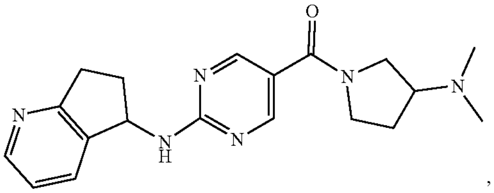
,
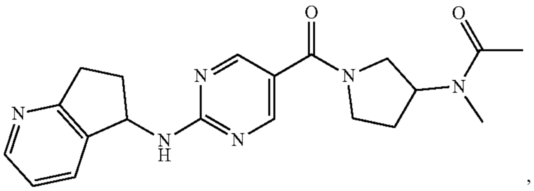
,
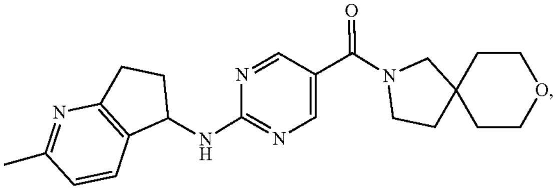
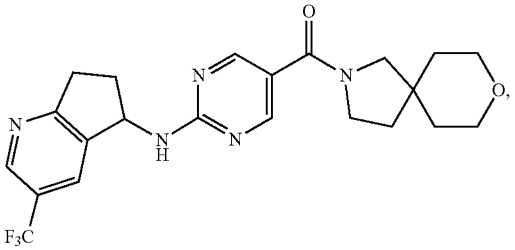

-continued
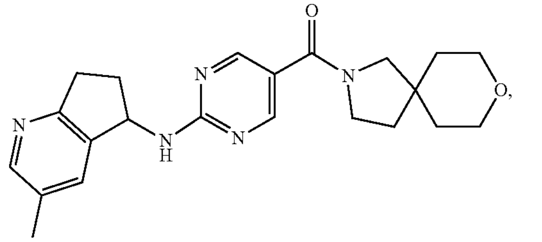
,
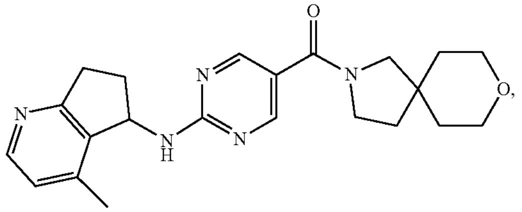
,
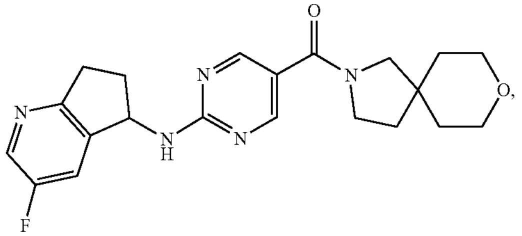
,
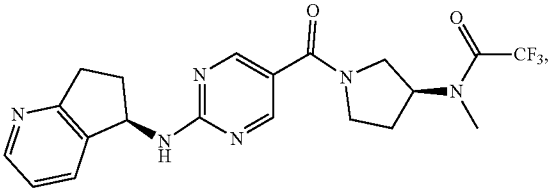
,
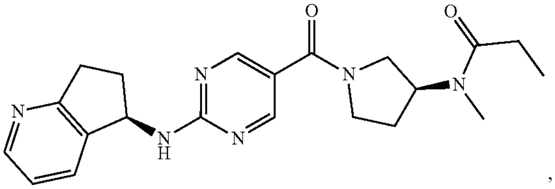
,
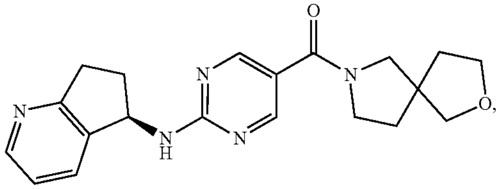
,
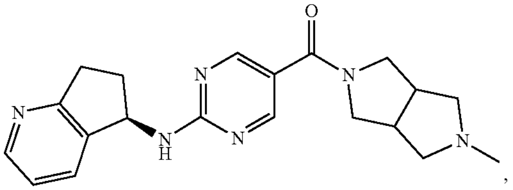
,
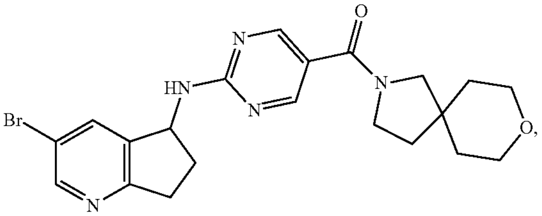
,
-continued
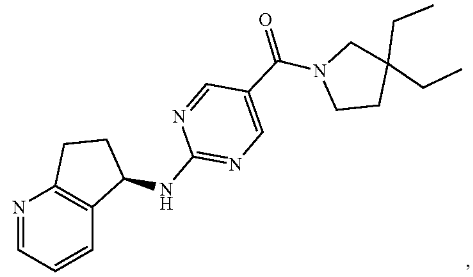
,
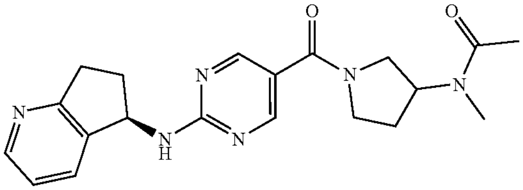
or
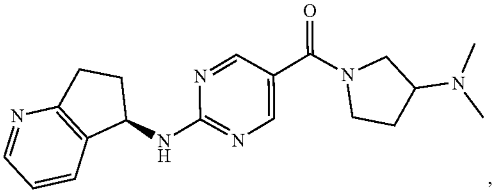
,
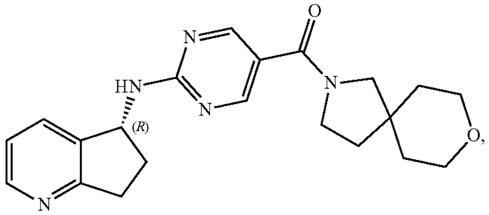
,
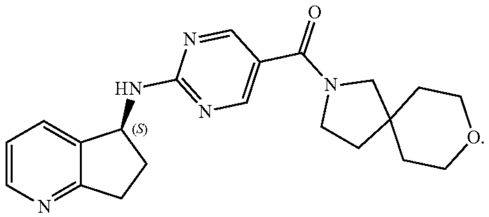
.
In some preferred embodiments of the present disclosure, the pyrimidine carboxamide compound represented by formula I is any one of the following structures:
Compound
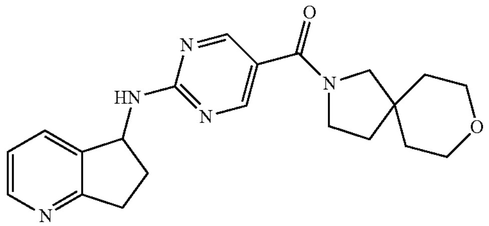

-continued

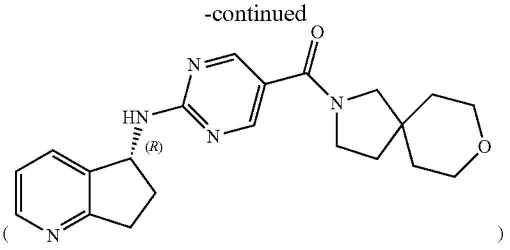

with a retention time of 8.483 min under the following conditions: chiral chromatographic resolution, chromatographic column: CHIRALPAK AD-H, 250×4.6 mm, 5 μm; column temperature: 35° C.; flow rate: 0.4 mL/min; wavelength: 254 nm; gradient: A: n-hexane, B: isopropanol, A:B=1:4; run time: 50 min;

compound

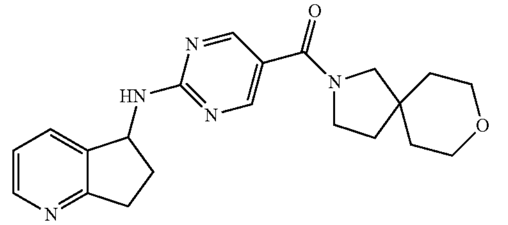

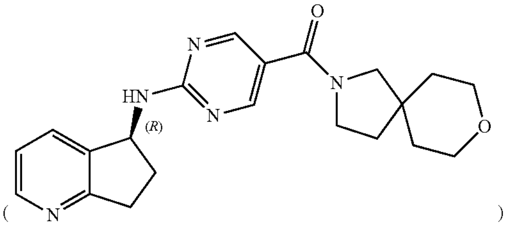

with a retention time of 13.580 min under the following conditions: chiral chromatographic resolution, chromatographic column: CHIRALPAK AD-H, 250×4.6 mm, 5 μm; column temperature: 35° C.; flow rate: 0.4 mL/min; wavelength: 254 nm; gradient: A: n-hexane, B: isopropanol, A:B=1:4; run time: 50 min. It should be understood by those skilled in the art that the absolute configuration of the compound is only distinguished by retention time, and the absolute configurations corresponding to different retention times are subject to actual conditions.

In the present disclosure, the pyrimidine carboxamide compound represented by formula I or the pharmaceutically acceptable salt thereof may have one or more chiral carbon atoms, and thus can be separated to obtain optically pure isomers, such as pure enantiomers, or racemates, or mixed isomers. Pure single isomers can be obtained by separation methods in the art, such as salt formation by chiral crystallization, or chiral preparative column separation.

In the present disclosure, if a stereoisomer of the pyrimidine carboxamide compound represented by formula I or the pharmaceutically acceptable salt thereof exists, the pyrimidine carboxamide compound may exist as a single stereoisomer or a mixture thereof (such as racemate). The term "stereoisomer" refers to cis-trans isomers or optical isomers. Such stereoisomers can be separated, purified and enriched by asymmetric synthetic methods or chiral separation methods (including but not limited to thin-layer chromatography, rotary chromatography, column chromatography, gas chromatography, high-pressure liquid chromatography, etc.), and can also be obtained by chiral resolution through bond formation (chemical bonding, etc.) or salt formation (physical bonding, etc.) with other chiral compounds. The term "single stereoisomer" means that the mass content of one stereoisomer of the compound of the present disclosure relative to all stereoisomers of the compound is not less than 95%.

Accordingly, throughout the description, those skill in the art may select the groups and substituents thereof in the pyrimidine carboxamide compounds represented by formula I, or the tautomers, mesomers, racemates, enantiomers, diastereomers thereof, or the mixture forms thereof, or the pharmaceutically acceptable salts thereof, so as to provide stable pyrimidine carboxamide compounds represented by formula I, or tautomers, mesomers, racemates, enantiomers, diastereomers thereof, or mixture forms thereof, or pharmaceutically acceptable salts thereof, including but not limited to the compounds in the embodiments of the present disclosure.

The pyrimidine carboxamide compounds represented by formula I, or the tautomers, mesomers, racemates, enantiomers, diastereomers thereof, or the mixture forms thereof, or the pharmaceutically acceptable salts thereof of the present disclosure may be synthesized by methods including the methods similar to those well known in the field of chemistry, whose steps and conditions can refer to the steps and conditions of similar reactions in the art, in particular according to the description herein. Starting materials are generally available from commercial sources such as Aldrich or can be readily prepared using methods well known to those skilled in the art (available via SciFinder and Reaxys online databases).

In the present disclosure, the pyrimidine carboxamide compounds represented by formula I, or the tautomers, mesomers, racemates, enantiomers, diastereomers thereof, or the mixture forms thereof, or the pharmaceutically acceptable salts thereof, may also be obtained through peripheral modification of the prepared pyrimidine carboxamide compounds represented by formula I, or the tautomers, mesomers, racemates, enantiomers, diastereomer thereof, or the mixture forms thereof, or the pharmaceutically acceptable salts thereof, using conventional methods in the art, so as to obtain the other pyrimidine carboxamide compounds represented by formula I, or the tautomers, mesomers, racemates, enantiomers, diastereomers thereof, or the mixture forms thereof, or the pharmaceutically acceptable salts thereof.

Generally, the compounds of the present disclosure can be prepared by the methods described herein, unless further specified, the definitions of substituents are as shown in formula I. The following reaction schemes and embodiments serve to further illustrate the present disclosure.

The raw materials or reagents necessary for the preparation of compounds represented by formula I are commercially available or can be prepared by synthetic methods known in the art. The compounds of the present disclosure can be prepared as a free base or as a salt thereof with the addition of an acid, as described in the experimental section below. The term pharmaceutically acceptable salt refers to a pharmaceutically acceptable salt as defined herein and has all the pharmaceutical activities of the parent compound. A pharmaceutically acceptable salt can be prepared by adding the corresponding acid to a suitable organic solvent of an organic base according to conventional methods.

Examples of salt formation include: salt formation with inorganic acids, such as hydrochloric acid, hydrobromic acid, sulfuric acid, nitric acid, phosphoric acid; and salt formation with organic acids, such as acetic acid, benzenesulfonic acid, benzoic acid, camphorsulfonic acid, citric acid, ethanesulfonic acid, fumaric acid, glucoheptonic acid, glutamic acid, glycolic acid, hydroxynaphthoic acid, 2-hydroxyethanesulfonic acid, lactic acid, maleic acid, malic acid, malonic acid, mandelic acid, methanesulfonic acid, hexadienedioic acid, 2-naphthalenesulfonic acid, propionic acid, salicylic acid, succinic acid, tartaric acid, p-toluenesulfonic acid or pivalic acid.

The pyrimidine carboxamide compound represented by formula I may have one or more chiral carbon atoms, and thus can be separated to obtain optically pure isomers, such as pure enantiomers, or racemates, or mixed isomers. Pure single isomers can be obtained by separation methods in the art, such as salt formation by chiral crystallization, or chiral preparative column separation.

The chemicals used in the synthetic route described herein include solvents, reagents, catalysts, protecting groups and deprotecting groups, and the protecting groups include tert-butoxycarbonyl (Boc). The above methods may additionally include steps before or after the steps specifically described herein, wherein suitable protecting groups may be added or removed to obtain the target compound. In addition, various synthetic steps can be performed alternately or sequentially to obtain the final target product.

The present disclosure provides a pharmaceutical composition, comprising the pyrimidine carboxamide compound represented by formula I, or the tautomer, mesomer, racemate, enantiomer, diastereomer thereof, or the mixture form thereof, or the pharmaceutically acceptable salt thereof, and, (one or more) pharmaceutical excipients (such as pharmaceutically available carriers, diluents, vehicles or other vehiculums). The dose of the pyrimidine carboxamide compound represented by formula I, or the tautomer, mesomer, racemate, enantiomer, diastereomer thereof, or the mixture form thereof, or the pharmaceutically acceptable salt thereof may be a therapeutically effective amount.

The present disclosure also provides a use of the pyrimidine carboxamide compound represented by formula I, or the tautomer, mesomer, racemate, enantiomer, diastereomer thereof, or the mixture form thereof, or the pharmaceutically acceptable salt thereof in the manufacture of a Vanin-1 inhibitor. In the use, the Vanin-1 inhibitor can be used in vivo in mammals; it can also be used in vitro, mainly for experimental purposes, for example, it can be used as a standard sample or control sample to provide a comparison, or made into a kit according to conventional methods in the art to provide a rapid detection for the inhibitory effect of Vanin-1. The term "Vanin-1 (enzyme) inhibitor" as used herein refers to a compound that binds to Vanin-1 (enzyme) and reduces the resulting enzyme activity.

The present disclosure also provides a use of the pyrimidine carboxamide compound represented by formula I, or the tautomer, mesomer, racemate, enantiomer, diastereomer thereof, or the mixture form thereof, or the pharmaceutically acceptable salt thereof in the manufacture of a drug; the drug may be used to prevent and/or treat diseases related to Vanin-1, or, the drug may be used to prevent and/or treat one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases; for another example, a drug for Crohn's disease, inflammatory bowel disease and ulcerative colitis. The diseases related to Vanin-1 may comprise one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases; for another example, inflammatory bowel disease, ulcerative colitis, Crohn's disease, colorectal cancer and gastritis.

Another aspect of the present disclosure relates to a method for preventing and/or treating diseases related to Vanin-1, comprising administering to a patient a therapeutically effective amount of the pyrimidine carboxamide compound represented by formula I, or the tautomer, mesomer, racemate, enantiomer, diastereomer thereof, or the mixture form thereof, or the pharmaceutically acceptable salt thereof, or the pharmaceutical composition comprising the same. For example, the treatment of a disease or condition mediated by or otherwise associated with inhibition of Vanin-1 enzyme. For example, one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases; for another example, inflammatory bowel disease, ulcerative colitis, Crohn's disease, colorectal cancer and gastritis.

Another aspect of the present disclosure relates to a method for preventing and/or treating one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases (such as inflammatory bowel disease, ulcerative colitis, Crohn's disease, colorectal cancer and gastritis), comprising administering to a patient a therapeutically effective amount of the pyrimidine carboxamide compound represented by formula I, or the tautomer, mesomer, racemate, enantiomer, diastereomer thereof, or the mixture form thereof, or the pharmaceutically acceptable salt thereof, or the pharmaceutical composition comprising the same.

Another aspect of the present disclosure relates to a drug for inhibiting Vanin-1, comprising the pyrimidine carboxamide compound represented by formula I, or the tautomer, mesomer, racemate, enantiomer, diastereomer thereof, or the mixture form thereof, or the pharmaceutically acceptable salt thereof, or the pharmaceutical composition comprising the same.

The compounds of the present disclosure may be administered topically or systemically, for example, by enteral administration, such as rectal or oral administration, or by parenteral administration to mammals (in particular to humans). The compounds of the present disclosure may also be administered parenterally, for example, by inhalation, injection or infusion, such as by intravenous, intraarterial, intraosseous, intramuscular, intracerebral, extraventricular, intrasynovial, intrasternal, intrathecal, intralesional, intracranial, intratumoral, intradermal and subcutaneous injection or infusion.

The effective amount of the compounds, pharmaceutical compositions or drugs of the present disclosure depends on the species, body weight, age, individual condition, individual pharmacokinetic parameters, disease to be treated and mode of administration of mammals.

The effective amount of the compounds, pharmaceutical compositions or drugs of the present disclosure can be readily determined by conventional experiments, and the most effective and convenient route of administration and the most appropriate formulation can also be determined by conventional experiments.

The pharmaceutical excipients may be those widely used in the field of pharmaceutical production. Excipients are mainly used to provide a safe, stable and functional pharmaceutical composition, and may also provide a method to allow the active ingredients to dissolve at a desired rate after the subject receives administration, or to facilitate effective absorption of the active ingredients after the subject receives administration of the composition. The pharmaceutical excipients may be inert fillers, or provide a certain function, such as stabilizing the overall pH value of the composition or preventing the degradation of the active ingredients of the composition. The pharmaceutical excipients may comprise one or more of the following excipients: binders, suspending agents, emulsifiers, diluents, fillers, granulating agents, adhesives, disintegrants, lubricants, anti-adhesive agents, glidants, wetting agents, gelling agents, absorption retarders, dissolution inhibitors, enhancers, adsorbents, buffers, chelators, preservatives, coloring agents, corrigents and sweetening agents.

Substances which may be used as pharmaceutically acceptable excipients include, but are not limited to, ion exchangers, aluminum, aluminum stearate, lecithin, serum proteins such as human serum albumin, buffer substances such as phosphates, glycine, sorbic acid, potassium sorbate, partial glyceride mixture of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, polyacrylates, waxes, polyethylene-polyoxypropylene block polymers, lanolin, sugars such as lactose, glucose and sucrose; starches such as corn starch and potato starch; cellulose and derivatives thereof such as sodium carboxymethyl cellulose, ethyl cellulose and cellulose acetate; gum powder; malt; gelatin; talc; excipients such as cocoa butter and suppository waxes; oils such as peanut oil, cottonseed oil, safflower oil, sesame oil, olive oil, corn oil and soybean oil; diol compounds such as propylene glycol and polyethylene glycol; esters such as ethyl oleate and ethyl laurate; agar; buffers such as magnesium hydroxide and aluminum hydroxide; alginic acid; pyrogen-free water; isotonic salts; Ringer's solution; ethanol, phosphate buffer solution, and other nontoxic suitable lubricants such as sodium dodecyl sulfate and magnesium stearate, coloring agents, release agents, coatings, sweetening agents, flavoring agents and fragrances, preservatives and antioxidants.

The pharmaceutical compositions of the present disclosure may be prepared according to the disclosure using any method known to those skilled in the art. For example, conventional mixing, dissolving, granulating, emulsifying, milling, encapsulating, entrapping or freeze-drying processes.

Pharmaceutical dosage forms of the compounds of the present disclosure may be provided in the form of immediate release, controlled release, sustained release or targeted drug release systems. Common dosage forms include, for example, solutions and suspensions, (micro)emulsions, ointments, gels and patches, liposomes, tablets, dragees, soft- or hard-shell capsules, suppositories, ovules, implants, amorphous or crystalline powders, aerosols and lyophilized formulations. Depending on the route of administration used, special devices may be needed to administer or give the drug, such as syringes and needles, inhalers, pumps, injection pens, applicators or specialflasks. Pharmaceutical dosage forms often consist of a drug, an excipient and a container/closure system. One or more excipients (also known as inactive ingredients) may be added to the compounds of the present disclosure to improve or facilitate the manufacture, stability, administration and safety of the drug, and may provide methods for obtaining the desired drug release profile. Therefore, the type of excipients added to the drug may depend on various factors such as the physical and chemical properties of the drug, route of administration, and preparation steps. Pharmaceutical excipients exist in the art and include those listed in various pharmacopoeias. (See U.S. Pharmacopoeia (USP), Japanese Pharmacopoeia (JP), European Pharmacopoeia (EP) and British Pharmacopoeia (BP); the U.S. Food and Drug Administration (www.fda-.gov) Center for Drug Evaluation and Research (CEDR) publications such as "Inactive Ingredient Guide" (1996); "Hand book of Pharmaceutical Additives" by Ash and Ash (2002, Synapse Information Resources, Inc., Endicott NY; etc.).

Pharmaceutical dosage forms of the compounds of the present disclosure may be manufactured by any of the methods well known in the art, for example by conventional mixing, sieving, dissolving, melting, granulating, dragee-making, tabletting, suspending, extruding, spray-drying, milling, emulsifying, (nano-/micro-) encapsulating, entrapping or freeze-drying processes.

The pharmaceutical compositions of the present disclosure may be administered topically or systemically, for example, by enteral administration, such as rectal or oral administration, or by parenteral administration to mammals (in particular to humans), and comprise a therapeutically effective amount of the compound or the pharmaceutically acceptable salt thereof of the present disclosure as an active ingredient, together with a pharmaceutically acceptable excipient, such as a pharmaceutically acceptable carrier. The therapeutically effective amount of the active ingredients is as defined in the context, and depends on the species, body weight, age, individual condition, individual pharmacokinetic parameters, disease to be treated and mode of administration of mammals. For enteral administration, such as oral administration, the compounds of the present disclosure may be formulated into a wide variety of dosage forms.

The pharmaceutical compositions and dosage forms may comprise one or more compounds of the present disclosure or one or more pharmaceutically acceptable salts thereof as active ingredients. The pharmaceutically acceptable carrier may be a solid or a liquid. Formulations in solid form include powders, tablets, pills, lozenges, capsules, cachets, suppositories and dispersible granules. The solid carrier can also be one or more substances which act as diluents, flavoring agents, solubilizers, lubricants, suspending agents, binders, preservatives, tablet disintegrants or encapsulating materials. In powders, the carrier is usually a finely divided solid, which is a mixture with the finely divided active component. In tablets, the active component is usually mixed with a carrier having the necessary adhesive capacity in suitable proportions and compacted into the desired shape and size. Suitable carriers include, but are not limited to, magnesium carbonate, magnesium stearate, talc, sugar, lactose, pectin, dextrin, starch, gelatin, methyl cellulose, sodium carboxymethyl cellulose, low melting point wax, cocoa butter and the like. Formulations of the active compounds may comprise an encapsulating material as a carrier, providing a capsule in which the active component, with or without a carrier, is surrounded by a carrier bound thereto.

Other forms suitable for oral administration include formulations in liquid form, including emulsions, syrups, elixirs, aqueous solutions, aqueous suspensions, or formulations in solid form intended to be converted to formulations in liquid form shortly before use. Emulsions may be prepared in solutions, for example, in propylene glycol aqueous solutions, or may contain emulsifiers such as lecithin, sorbitan monooleate, or Arabic gum. Aqueous solutions may be prepared by dissolving the active component in water and adding suitable coloring agents, fragrances, stabilizers and thickening agents. Aqueous suspensions may be prepared by dispersing the finely divided active ingredients in water with binders such as natural or synthetic gums, resins, methyl cellulose, carboxymethyl cellulose and other commonly used suspending agents. Formulations in solid form include solutions, suspensions and emulsions, and may also contain coloring agents, fragrances, stabilizers, buffers, artificial and natural sweetening agents, dispersing agents, thickening agents, solubilizers and the like, in addition to the active component.

Exemplary compositions for rectal administration include suppositories, which may contain, for example, a suitable non-irritating excipient, such as cocoa butter, synthetic glyceride, or polyethylene glycol, which is a solid at room temperature, but melts and/or dissolves in the rectal lumen to release the drug.

The therapeutically effective amount may be first estimated using various methods well known in the art. The initial dose for animal studies can be based on the effective concentration established in cell culture assays. The dose range suitable for individuals can be determined, for example, using data obtained from animal studies and cell culture assays. In certain embodiments, the compounds of the present disclosure may be prepared as agents for oral administration.

The effective amount or therapeutically effective amount or dose of an agent (for example, the compound of the present disclosure) refers to the amount of the agent or compound that results in amelioration of symptoms or prolongation of survival in an individual. Toxicity and therapeutic efficacy of the molecules can be determined by standard pharmaceutical procedures in cell cultures or laboratory animals, for example by measuring the $LD_{50}$ (the dose lethal to 50% of the population) and the $ED_{50}$ (the dose therapeutically effective in 50% of the population). The dose ratio between toxic and therapeutic effects is the therapeutic index and it can be expressed as $LD_{50}/ED_{50}$. Agents which exhibit high therapeutic indices are preferred.

The effective amount or therapeutically effective amount refers to the amount of the compound or pharmaceutical composition that will elicit the biological or medical response in a tissue, system, animal, or human that is being sought by the researcher, veterinarian, physician, or other clinician. The dose is preferably within a range of circulating concentrations that include the $ED_{50}$ with little or no toxicity. The dose may vary within this range depending upon the dosage form utilized and/or the route of administration utilized. The proper formulation, route of administration, dose and interval of administration should be selected according to methods known in the art, taking into account the characteristics of individual conditions.

The dose and interval may be individually adjusted to provide levels in plasma of the active moiety sufficient to obtain the desired effect; that is, the minimum effective concentration (MEC). The MEC will vary for each compound, but can be estimated, for example, from in vitro data and animal experiments. The dose necessary to obtain the MEC will depend on individual characteristics and route of administration. In cases of topical administration or selective uptake, the effective local concentration of the drug may not be related to plasma concentration.

The amount of the agent or composition administered may depend on various factors, including the sex, age and weight of the individual to be treated, the severity of the condition, the mode of administration, and the judgment of the prescribing physician.

If desired, the compositions of the present disclosure may be provided in packaging or dispensing devices containing one or more unit dosage forms (containing the active ingredients). For example, the packaging or dispensing device may comprise metal or plastic foil (such as foam packaging), or glass and rubber stoppers, such as in vials. The packaging or dispensing device may be accompanied by instructions for administration. Compositions comprising the compounds of the present disclosure formulated in compatible pharmaceutical carriers may also be prepared, placed in appropriate containers, and labeled for treatment of specified symptoms.

Unless otherwise specified, all technical and scientific terms as used herein have the standard meaning in the art to which the claimed subject matter pertains. If a term has more than one definition, the definition herein shall prevail.

Group Definition

Unless otherwise specified, the following definitions as used herein shall apply. For the purposes of the present disclosure, the chemical elements correspond to the Periodic Table of the Elements, CAS Edition, and "Handbook of Chemistry and Physics", 75th Edition, 1994. In addition, general principles of organic chemistry can be found in the description of "Organic Chemistry", Thomas Sorrell, University Science Books, Sausalito:1999, and "March's Advanced Organic Chemistry" by Michael B. Smith and Jerry March, John Wiley & Sons, New York: 2007, the entire contents of which are incorporated herein by reference.

In the present description, groups and substituents thereof may be selected by those skilled in the art to provide stable structural moieties and compounds. When a substituent is described by a conventional chemical formula written from left to right, the substituent also includes the chemically equivalent substituent obtained when the structural formula is written from right to left.

Certain chemical groups defined herein are preceded by abbreviated notations to indicate the total number of carbon atoms present in the group. For example, $C_1$-$C_6$ alkyl refers to an alkyl having a total of 1, 2, 3, 4, 5 or 6 carbon atoms as defined below. The total number of carbon atoms in the abbreviated notation does not include the carbon that may be present in the substituent of the group.

The numerical range defined in the substituents of the present disclosure, such as 0-4, 1-4, 1-3 and the like, indicates integers within the range, for example, 1-6 refers to 1, 2, 3, 4, 5, 6.

In addition to the foregoing, when used in the description and claims of the present disclosure, the following terms have the meanings shown below unless otherwise specified.

The term "include" is open-ended, that is, it includes what is specified in the present disclosure, but does not exclude other aspects.

The term "substituted" means that one or more hydrogen atoms on a specific atom are substituted by the substituent, including deuterium and hydrogen variables, as long as the valence of the specific atom is normal and the substituted compound is stable.

In general, the term "substituted" means that one or more hydrogen atoms in a given structure are substituted by specific substituents. Further, when the group is substituted by the one or more substituents, the substituents are independent of each other, that is, the one or more substituents may be different from each other or identical. Unless otherwise specified, a substituent may substitute at each substitutable position of the group being substituted. When more than one position in a given structural formula can be substituted by one or more substituents selected from specific groups, then the substituents can be substituted equally or differently at each position.

In various sections of the description, the substituents of the disclosed compounds of the present disclosure are disclosed according to the type or range of the groups. In particular, it is noted that the present disclosure includes each independent sub-combination of the individual members of the types and ranges of such groups. For example, the term "$C_1$-$C_6$ alkyl" or "$C_{1-6}$ alkyl" specifically refers to independently disclosed methyl, ethyl, $C_3$ alkyl, $C_4$ alkyl, $C_5$ alkyl and $C_6$ alkyl; "$C_1$-4 alkyl" specifically refers to independently disclosed methyl, ethyl, $C_3$ alkyl (i.e., propyl, including n-propyl and isopropyl) and $C_4$ alkyl (i.e., butyl, including n-butyl, isobutyl, sec-butyl and tert-butyl).

The term "halogen" is selected from F, Cl, Br or I, and refers in particular to F or Cl.

In the present disclosure, the term "alkyl", as a group or part of another group, refers to a saturated aliphatic hydrocarbon group, which is a straight or branched chain group containing 1 to 12 carbon atoms, preferably a straight or branched chain alkyl containing 1 to 6 carbon atoms. The general formula is $C_nH_{2n+1}$. The term "$C_1$-$C_6$ alkyl" means that the alkyl moiety contains 1, 2, 3, 4, 5 or 6 carbon atoms. In a certain embodiment, the term "alkyl" refers to $C_1$-$C_6$ alkyl. In a certain embodiment, the term "alkyl" refers to $C_1$-$C_4$ alkyl.

Non-limiting examples of lower alkyl containing 1 to 6 carbon atoms include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. Non-limiting examples of lower alkyl containing 1 to 12 carbon atoms include the above examples of lower alkyl containing 1 to 6 carbon atoms, as well as 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched chain isomers thereof and the like.

In the present disclosure, as a group or part of another group, unless otherwise specified, the term "cycloalkyl" refers to a saturated monocyclic, polycyclic or bridged carbocyclic substituent consisting only of carbon atoms and hydrogen atoms, and it may be connected to the rest of the molecule by a single bond via any suitable carbon atom; in the case of a polycyclic cycloalkyl, it may be a bridged ring or spiro ring system with a fused ring or spiro ring connection (that is, two gem-hydrogens on a carbon atom are substituted by an alkylene). Cycloalkyl substituents may be connected to the central molecule via any suitable carbon atom. In some embodiments, a ring having 3 to 10 carbon atoms may be represented as $C_3$-$C_{10}$ cycloalkyl. In some embodiments, $C_3$-$C_6$ cycloalkyl includes cyclopropyl ($C_3$), cyclobutyl ($C_4$), cyclopentyl ($C_5$) and cyclohexyl ($C_6$). In some embodiments, examples of $C_3$-$C_{10}$ cycloalkyl include the above $C_3$-$C_6$ cycloalkyl groups together with cycloheptyl ($C_7$), cyclooctyl ($C_8$), cyclononyl ($C_9$) and cyclodecyl ($C_{10}$).

In the present disclosure, the term "heterocycloalkyl", as a group or part of another group, refers to a stable 3- to 7-membered saturated cyclic group consisting of 2 to 6 carbon atoms as well as 1 to 4 heteroatoms selected from nitrogen, oxygen and sulfur. Exemplary 3-membered heterocycloalkyl includes, but is not limited to, aziridinyl, oxiranyl, and thiacyclopropanyl, or a stereoisomer thereof; exemplary 4-membered heterocycloalkyl includes, but is not limited to, azetidinyl, epoxypropanyl, thietanyl, or an isomer and a stereoisomer thereof; exemplary 5-membered heterocycloalkyl includes, but is not limited to, tetrahydrofuranyl, tetrahydrothienyl, pyrrolidinyl, thiazolidinyl, isothiazolidinyl, oxazolidinyl, isoxazolidinyl, imidazolidinyl, pyrazolidinyl, dioxolanyl, oxathiofuranyl, dithiofuranyl, or an isomer and a stereoisomer thereof. Exemplary 6-membered heterocycloalkyl includes, but is not limited to, piperidinyl, tetrahydropyranyl, thiacyclopentyl, morpholinyl, thiomorpholinyl, dithianyl, dioxanyl, piperazinyl, triazinyl, or an isomer and a stereoisomer thereof; exemplary 7-membered heterocycloalkyl includes, but is not limited to, azepanyl, oxepanyl, thiepanyl, and diazepanyl, or an isomer and a stereoisomer thereof. In a certain embodiment, "heterocycloalkyl" is $C_2$-$C_5$ heterocycloalkyl, wherein the heteroatom is selected from one or more of N, O and S, and the number of heteroatoms is 1, 2 or 3.

In the present disclosure, the term "heteroaryl", as a group or part of another group, refers to a group ("4- to 16-membered heteroaryl") of 4- to 16-membered monocyclic or bicyclic 4n+2 aromatic ring system (for example, with 6 or 10 shared p-electrons in a cyclic array), having carbon atoms as well as 1 to 3 heteroatoms (each of which is independently selected from nitrogen, oxygen and sulfur) provided in the aromatic ring system. In heteroaryl groups containing one or more nitrogen atoms, the point of connection can be a carbon or nitrogen atom, as valency permits.

In some embodiments, the heteroaryl is a 4- to 6-membered heteroaryl with 1 to 3 heteroatoms selected from one or more of N, O and S, preferably a 5- to 6-membered heteroaryl.

Exemplary 5-membered heteroaryl groups include, but are not limited to: pyrrolyl, furyl, thienyl, imidazolyl, pyrazolyl, oxazolyl, isoxazolyl, thiazolyl, isothiazolyl, triazolyl, oxadiazolyl, thiadiazolyl, furyl, oxatriazolyl, or tetrazolyl. Exemplary 6-membered heteroaryl groups include, but are not limited to, pyridyl, pyrazinyl, pyridazinyl, pyrimidinyl, triazinyl, or tetrazinyl.

The terms "moiety", "structural moiety", "chemical moiety", "group", "chemical group" as used herein refer to a specific fragment or functional group in a molecule. Chemical moieties are generally considered to be chemical entities embedded or attached to molecules.

When the enumerative substituent does not indicate by which atom it is linked to the compound included but not specifically mentioned in a general chemical formula, such substituent can be bonded by any atom thereof. A combination of the substituent and/or the variant thereof is allowed only when the combination results in a stable compound.

In various sections of the present disclosure, linking substituents are described. When the structure clearly requires a linking group, the enumerative Markush variables for the group should be understood as linking groups. For example, if the structure requires a linking group and the Markush group definition for the variable enumerates “alkyl” or “aryl”, it should be understood that the “alkyl” or “aryl” represents a linked alkylene or arylidene group, respectively.

In some specific structures, when an alkyl group is clearly indicated as a linking group, the alkyl group represents a linked alkylene group, for example, $C_1$-$C_6$ alkyl in the group “halo-$C_1$-$C_6$ alkyl” should be understood as $C_1$-$C_6$ alkylene.

The term “alkylene” means a saturated divalent hydrocarbyl group obtained by removing two hydrogen atoms from a saturated straight or branched chain hydrocarbyl. Examples of alkylene groups include methylene ($-CH_2-$), ethylene {including $-CH_2CH_2-$ or $-CH(CH_3)-$}, isopropylidene {including $-CH(CH_3)CH_2-$ or $-C(CH_3)_2$-} and the like.

Unless otherwise specified, all technical and scientific terms as used herein have the standard meaning in the art to which the claimed subject matter pertains. If a term has more than one definition, the definition herein shall prevail.

Unless otherwise specified, it should be understood that the singular form used in the present disclosure, such as “a”, includes plural referents. In addition, the term “include” is open-ended and not closed, that is, it includes what is specified in the present disclosure, but does not exclude other aspects.

Unless otherwise specified, the present disclosure uses the conventional methods of mass spectrometry and elemental analysis, and the steps and conditions can be referred to the conventional operating steps and conditions in the art.

Unless otherwise specified, the present disclosure uses standard nomenclature and standard laboratory procedures and techniques of analytical chemistry, organic synthetic chemistry and optics. In some cases, standard techniques are used for chemical synthesis, chemical analysis, and performance testing of luminescent devices.

In addition, it should be noted that, unless otherwise clearly specified, the description “ . . . be independently” used in the present disclosure should be understood in a broad sense, which means that the described individuals are independent of each other and can be the same or different specific groups independently. In more detail, the description “ . . . be independently” can mean either that the specific options expressed between the same symbols in different groups do not affect each other; or that the specific options expressed between the same symbols in the same group do not affect each other.

It can be understood by those skilled in the art that, according to the convention used in the art, “  ”

used in the structural formula of the group described in the present disclosure means that the corresponding group is linked to other fragments and groups in the compound through this site.

“Pharmaceutically acceptable” means that which is useful in preparing a pharmaceutical composition that is generally safe and non-toxic, and is not biologically and otherwise undesirable, and includes that which is pharmaceutically acceptable for veterinary use as well as human use.

The term “excipient” refers to a pharmaceutically acceptable chemical substance, such as an agent known to those of ordinary skill in the pharmaceutical field for use in facilitating the administration of a drug. It is a compound that is useful in preparing a pharmaceutical composition that is generally safe and non-toxic, and is biologically or otherwise undesirable, and includes excipients that are pharmaceutically acceptable for veterinary use as well as human use. Typical excipients include binders, surfactants, diluents, disintegrants and lubricants.

The term “therapeutically effective amount” refers to the amount of a compound used which, when administered to a subject to treat a disease state, is sufficient to achieve such treatment of the disease state. The “therapeutically effective amount” will vary according to the compound, the disease state being treated, the severity of the disease being treated, the age and relative health of the subject, the route and mode of administration, the judgment of the attending physician or veterinarian, and the like.

The term “mammal” refers to a human or any mammal such as a primate, farm animal, pet animal or laboratory animal. Examples of such animals are monkeys, cows, sheep, horses, pigs, dogs, cats, rabbits, mice and rats, and the like. Mammals are preferably humans.

The above preferred conditions can be combined arbitrarily to obtain preferred embodiments of the present disclosure without violating common knowledge in the art.

The reagents and raw materials used in the present disclosure are all commercially available.

The positive effect of the present disclosure is that a pyrimidine carboxamide compound is provided, which can be used as an inhibitor of Vanin enzyme, especially an inhibitor of Vanin-1; and it can be used to prevent and/or treat Crohn’s disease, ulcerative colitis and inflammatory bowel disease.

DETAILED DESCRIPTION

The present disclosure is further illustrated below by means of embodiments, but the present disclosure is not thereby limited to the scope of the embodiments. Experimental methods for which specific conditions are not specified in the following embodiments are selected according to conventional methods and conditions, or according to the trade description.

Example 1: Synthesis of Compound 1

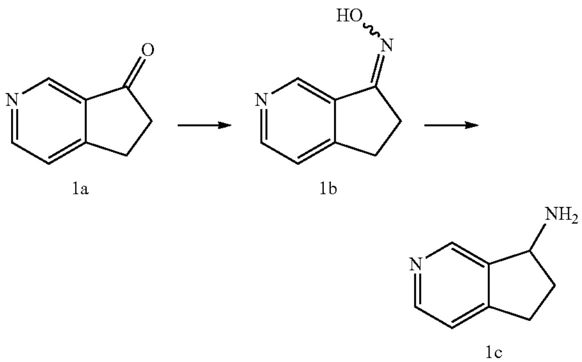

1a 1b 1c

-continued

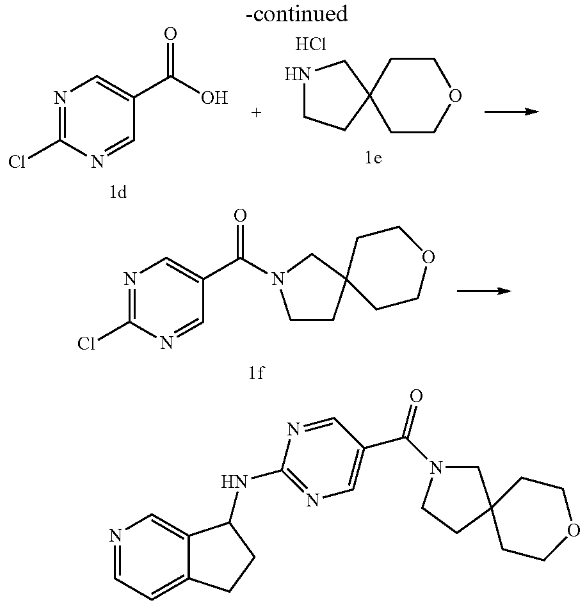

1d 1e 1f 1

Step 1

To a solution of compound 1a (250 mg) in ethanol/water (v/v=4:1, 5 mL) mixed solvent was added successively sodium acetate (129 mg) and hydroxylamine hydrochloride (322 mg). The resulting reaction mixture was heated to 94° C. and stirred for 2 hours. The reaction was completed. The reaction mixture was cooled, added with water (50 mL), and then extracted with ethyl acetate (100 mL×3). The organic phases were combined, dried over anhydrous sodium sulfate, filtered, and the filtrate was concentrated to obtain a crude product of compound 1b (257 mg).

Step 2

To a solution of compound 1b (257 mg) in acetic acid (5 mL) was added zinc powder (339 mg) in batches. The resulting reaction mixture was heated to 70° C. and stirred for 2 hours. The reaction was completed. The reaction mixture was cooled, and filtered through diatomite. The filtrate was concentrated, added with NaOH aqueous solution (10%) to adjust the pH to 9, and then extracted with ethyl acetate (20 mL×4). The organic phases were combined, dried over anhydrous sodium sulfate, filtered, and concentrated to obtain a crude product of compound 1c (100 mg).

Step 3

To a solution of compound 1d (25.40 g), compound 1e (31.00 g) and triethylamine (61.00 g) in acetonitrile (250 mL) was slowly added dropwise $T_3P$ (propylphosphonic anhydride) (254.00 g) at −10° C. under nitrogen atmosphere. After the dropwise addition was completed, the reaction system was kept at −5° C. and reacted for 3 hours. The reaction was completed. The reaction mixture was added with water (300 mL) to quench, concentrated to remove the organic solvent, and the residue was stirred at 5° C. for 1 hour. A solid was precipitated, filtered, and the filter cake was washed with water (100 mL×1) and dried to obtain compound if (42.00 g) with a yield of 93%.

$^1$H NMR (400 MHz, $CDCl_3$) δ 8.80 (s, 2H), 3.81-3.57 (m, 7H), 3.36 (s, 1H), 1.93 (td, J=14.58, 7.25 Hz, 2H), 1.66 (t, J=5.35 Hz, 2H), 1.58 (dd, J=11.10, 4.64 Hz, 2H).

Step 4

A solution of compound if (168 mg), compound 1c (100 mg) and potassium carbonate (99 mg) in isopropanol/water (v/v=99:1, 2 mL) mixed solvent was heated to 85° C. and stirred continuously for 4 hours. The reaction was completed. The mixture was cooled, filtered, and the filter cake was rinsed with isopropanol (10 mL×2), concentrated, and the residue was purified by silica gel column (methanol/dichloromethane=0-100%) to obtain compound 1 (26 mg).

$^1$H NMR (400 MHz, MeOH-$d_4$) δ 8.60 (s, 2H), 8.44 (s, 1H), 8.36 (d, J=3.89 Hz, 1H), 7.37 (d, J=4.86 Hz, 1H), 5.75 (t, J=6.75 Hz, 1H), 3.66 (ddd, J=19.18, 16.47, 5.76 Hz, 6H), 3.54 (d, J=22.28 Hz, 2H), 3.16-3.09 (m, 1H), 2.98 (dd, J=16.74, 8.39 Hz, 1H), 2.71-2.57 (m, 1H), 2.05 (dd, J=12.89, 8.02 Hz, 1H), 1.93 (dd, J=15.51, 7.35 Hz, 2H), 1.73-1.51 (m, 4H).

LCMS (ESI), $[M+H]^+$=380.2

Example 2: Synthesis of Compound 2, Compound 2-1 and Compound 2-2

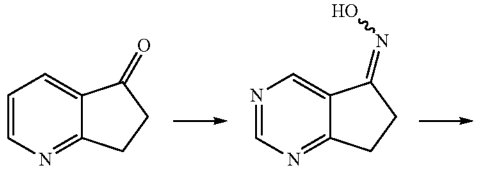

2a 2b

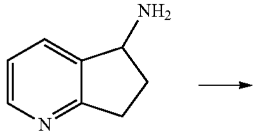

2c

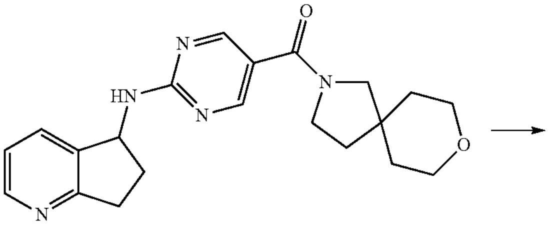

2

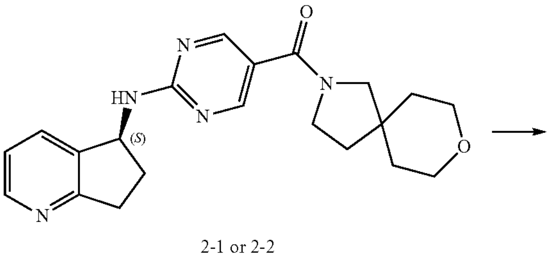

2-1 or 2-2

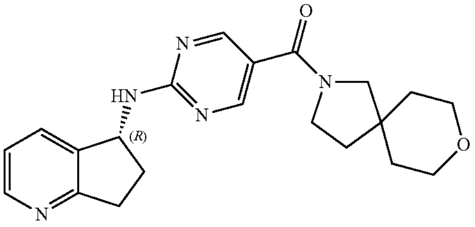

2-1 or 2-2

Step 1

To a solution of compound 2a (500 mg) in ethanol/water (v/v=4:1, 10 mL) mixed solvent was added successively sodium acetate (740 mg) and hydroxylamine hydrochloride (630 mg). The resulting reaction mixture was heated to 94° C. and stirred continuously for 2 hours. The reaction was completed. The reaction mixture was cooled, added with water (50 mL), and then extracted with ethyl acetate (30 mL×3). The organic phases were combined, dried over anhydrous sodium sulfate, filtered, and concentrated to obtain a crude product of compound 2b (500 mg).

Step 2

To a solution of compound 2b (320 mg) in acetic acid (6 mL) was added zinc powder (421 mg) in batches. The resulting reaction mixture was heated to 70° C. and stirred continuously for 2 hours. The reaction was completed. The mixture was cooled, filtered and concentrated. The reaction mixture was added with NaOH aqueous solution (10%) to adjust the pH to 9, and then extracted with ethyl acetate (20 mL×4). The organic phases were combined, dried over anhydrous sodium sulfate, filtered, and concentrated to obtain a crude product of compound 2c (100 mg).

Step 3

Compound 2 (66 mg) was obtained from compound if (168 mg) and compound 2c (100 mg) according to the method of Example 1.

$^1$H NMR (400 MHz, MeOH-$d_4$) δ 8.58 (s, 2H), 8.35 (d, J=4.69 Hz, 1H), 7.78-7.70 (m, 1H), 7.27-7.18 (m, 1H), 5.71 (t, J=7.15 Hz, 1H), 3.80-3.59 (m, 6H), 3.54 (d, J=20.77 Hz, 2H), 3.13 (ddd, J=16.55, 9.14, 3.68 Hz, 1H), 3.00 (td, J=16.84, 8.51 Hz, 1H), 2.67 (ddd, J=16.06, 8.24, 3.91 Hz, 1H), 2.14-1.99 (m, 1H), 1.93 (dd, J=16.94, 7.33 Hz, 2H), 1.72-1.51 (m, 4H).

LCMS (ESI), $[M+H]^+$=380.3

Two enantiomers 2-1 (retention time: 8.483 min) and 2-2 (retention time: 13.580 min) were obtained by chiral separation of compound 2.

The chromatographic conditions are as follows:

chromatographic column: CHIRALPAK AD-H (5 μm, 4.6×250 mm)

flow rate: 0.4 mL/min wavelength: 254 nm column temperature: 35° C.

mobile phase: A: n-hexane, B: isopropanol, A:B=1:4 run time: 50 min

Preparation Method of Compound 2-1

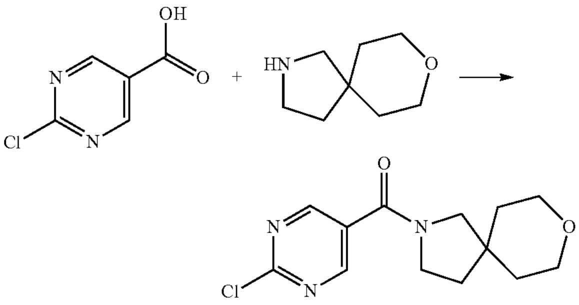

2-1f

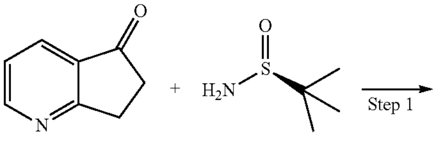

2-1a 2-1b

-continued

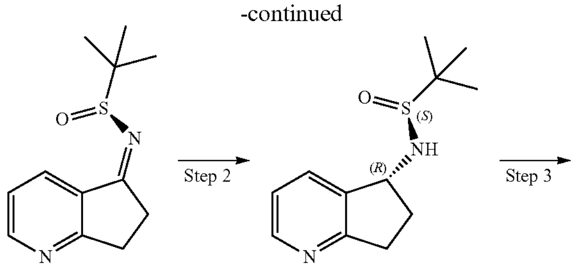

2-1c 2-1d

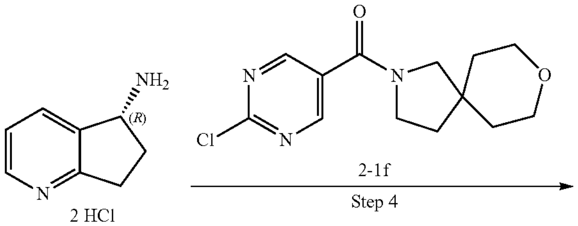

2 HCl
2-1e

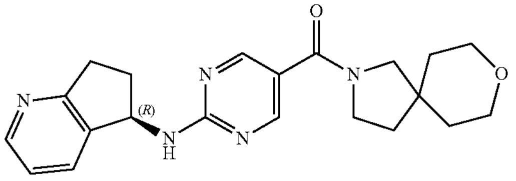

2-1

Preparation of Compound 2-1f

2-Chloropyrimidine-5-carboxylic acid (284 g, 1.78 mol) and 8-oxa-2-azaspiro[4.5]decane (310 g, 1.78 mol) were dissolved in dichloromethane, and the reaction mixture was cooled to −10° C., then $T_3P$ (625 g, 1.78 mol) was slowly added dropwise. After the addition was completed, the reaction mixture was reacted continuously at this temperature for 2 hours. After the complete of the reaction was detected by LCMS, the reaction mixture was added with water, stirred, and a solid was precipitated. The mixture was filtered and dried to obtain compound 2-1f (350 g, purity: 98%).

Step 1: Preparation of compound 2-1c

Compound 2-1b (385 g, 3.18 mol) and tetraethyl titanate (905 g, 3.97 mol) were dissolved in toluene (3 L), and the reaction mixture was heated to 110° C. under stirring, and refluxed; to the above reaction mixture was added dropwise a solution of compound 2-1a (352 g, 2.65 mol) in toluene (500 mL). After the dropwise addition was completed, the reaction mixture was heated at reflux continuously for 1 hour. After the reaction was completed, the reaction was stopped. The reaction mixture was cooled to room temperature, concentrated to remove the toluene, and the residue was added with water to quench, then added with ethyl acetate to extract the product. The reaction mixture was filtered through diatomite to remove the insoluble solid. The phases of the filtrate were separated, and the organic phases were collected, dried over anhydrous sodium sulfate, and concentrated to remove the solvent; the residue was dissolved with a small amount of MTBE, added with petroleum ether and stirred, and a solid was precipitated. The mixture was filtered, and the filtrate was concentrated to obtain compound 2-1c (500 g, yield: 80%).

Step 2: Preparation of Compound 2-1d

Compound 2-1c (500 g, 2.1 mol) was dissolved in 3000 mL of THF, and the reaction mixture was cooled to −60° C., then lithium tri-sec-butylborohydride (2510 mL, 2.51 mol) was slowly added dropwise. After the dropwise addition was completed, the reaction mixture was stirred at −60° C. After the reaction was completed, 100 mL of water was slowly added to quench. The mixture was extracted with ethyl acetate (500 mL×3). The organic phases were combined, washed with saturated sodium chloride solution (200 mL), and dried. The organic phase was distilled under reduced pressure to remove the solvent, and the crude product 2-1d was directly used in the next step.

Step 3: Preparation of Compound 2-1e

The crude product 2-1d was dissolved in 500 mL of methanol, and 200 mL of 4N HCl/MeOH was slowly added. The reaction was carried out at room temperature for 2 hours. After the reaction was completed, the reaction mixture was concentrated to obtain an oil, added with ethyl acetate, stirred and filtered to obtain compound 2-1e as a red solid powder (300 g, ee value: 92%, purity: 99%).

Step 4: Preparation of Compound 2-1

Compound 2-1e (284 g, 1.375 mol), compound 2-1f (350 g, 1.25 mol) and $K_2CO_3$ (862.5 g, 6.25 mol) were dissolved in isopropanol, and the reaction mixture was heated at reflux overnight. After the reaction was completed, the reaction mixture was cooled to room temperature. The reaction system was distilled under reduced pressure to remove the solvent, added with dichloromethane, stirred, and filtered. The filtrate was dissolved in 2 N HCl, and the pH of the aqueous phase was adjusted to 8 to 9 by adding 1 N NaOH. The mixture was extracted with dichloromethane, dried and concentrated to obtain compound 2-1.

$^1$H NMR (400 MHz, $CD_3OD$) δ 8.58 (s, 2H), 8.37 (d, J=5.1 Hz, 1H), 7.77 (s, 1H), 7.26 (d, J=2.5 Hz, 1H), 5.72 (t, J=7.7 Hz, 1H), 4.53 (s, 2H), 3.80-3.58 (m, 7H), 3.54 (d, J=18.8 Hz, 2H), 3.15 (ddd, J=16.9, 9.2, 3.7 Hz, 1H), 3.02 (dt, J=16.8, 8.5 Hz, 1H), 2.68 (dq, J=12.8, 4.4 Hz, 1H), 2.14-2.02 (m, 1H), 1.93 (q, J=8.1 Hz, 2H), 1.67 (d, J=5.8 Hz, 2H), 1.59 (d, J=5.7 Hz, 2H).

The absolute stereochemical configuration of compound 2-1 was determined by comparative determination of the above preparation method of the chiral compounds.

Example 3: Synthesis of Compound 7

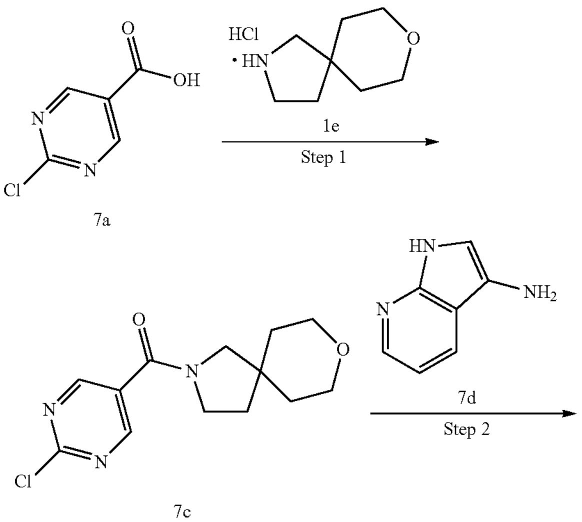

-continued

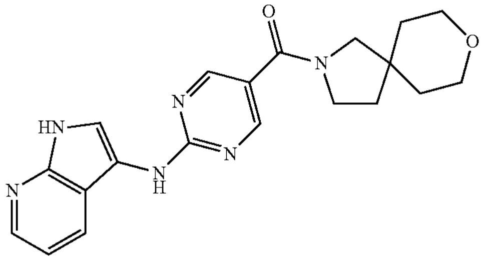

7

Step 1

To a 25 mL three-necked flask was added compound 7a (200 mg, 1.27 mmol), compound 1e (187 mg, 1.33 mmol) and acetonitrile (3 mL). The reaction mixture was cooled to −10° C., then $T_3P$ (350 mg, 0.4 mol) was slowly added dropwise. Then the reaction mixture was added with triethylamine (260 mg, 5.54 mmol) dissolved in acetonitrile (5 mL), and the reaction system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with 100 mL of water to obtain 200 mg of white solid as compound 7c with a yield of 56%.

Step 2

To a 10 mL three-necked flask was added successively compound 7c (200 mg, 0.71 mmol), compound 7d (100 mg, 0.75 mol) and isopropanol/water (V/V=99:1, 5 mL), and then added potassium carbonate (489 mg, 3.55 mmol). The reaction mixture was heated to 85° C. and stirred at reflux for 4 hours. After the reaction was completed, the system was cooled to 45° C., added with 5 mL of acetone, and stirred for 1 hour. The mixture was filtered and the filter cake was washed with 20 mL of acetone. The filtrate was concentrated to 3 mL, then added with 4 mL of isopropanol and concentrated to 2 mL, then cooled to 0° C. and stirred for 1 hour. The mixture was filtered to obtain 100 mg of off-white solid as compound 7 with a yield of 38%.

LCMS m/z (ESI): 379 [M+1].

$^1$H NMR (400 MHz, DMSO-$d_6$): δ 11.36 (s, 1H), 10.02 (s, 1H), 8.68 (d, J=1.6 Hz, 2H), 8.22 (m, 2H), 7.85 (s, 1H), 7.02-7.05 (m, 1H), 3.54-3.70 (m, 7H), 3.33-3.38 (m, 1H), 1.81 (s, 2H), 1.46-1.56 (m, 4H).

Example 4: Synthesis of Compound 8

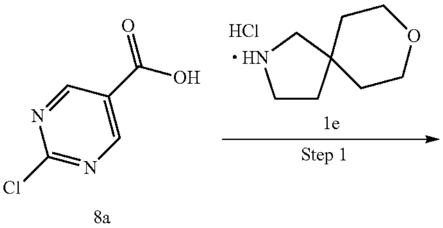

-continued

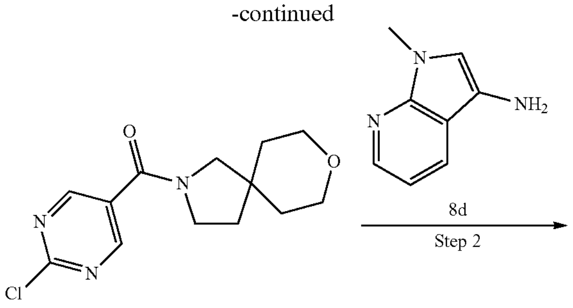

8c

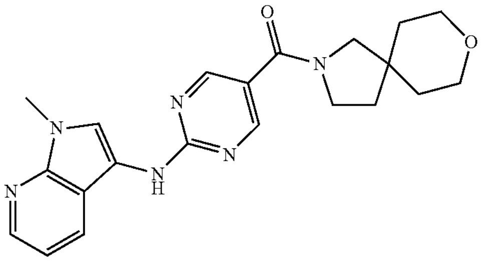

8

Step 1

To a 25 mL three-necked flask was added compound 8a (200 mg, 1.27 mmol), compound 1e (187 mg, 1.33 mmol) and acetonitrile (3 mL), and the reaction mixture was cooled to −10° C., then $T_3P$ (350 mg, 0.4 mol) was slowly added dropwise. The reaction mixture was added with triethylamine (260 mg, 5.54 mmol) dissolved in acetonitrile (5 mL), and the system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 200 mg of white solid as compound 8c with a yield of 56%.

Step 2

To a 10 mL three-necked flask was added compound 8c (90 mg, 0.32 mmol), compound 8d (50 mg, 0.34 mol) and isopropanol/water (v/v=99:1, 5 mL), and then added potassium carbonate (220 mg, 1.6 mmol). The reaction mixture was heated to 85° C. and stirred at reflux for 4 hours. After the reaction was completed, the reaction mixture was cooled to 45° C., added with acetone (5 mL), and stirred for 1 hour. The mixture was filtered and the filter cake was washed with acetone (20 mL). The filtrate was concentrated to 3 mL, then added with isopropanol (4 mL) and concentrated to 2 mL. The mixture was cooled to 0° C. and stirred for 1 hour. The mixture was filtered to obtain 40 mg of off-white solid as compound 8 with a yield of 32%.

LCMS m/z (ESI): 393 [M+1].

$^1$H NMR (400 MHz, DMSO-$d_6$): δ 10.11 (s, 1H), 8.68 (d, J=1.6 Hz, 2H), 8.22 (m, 2H), 7.94 (m, 1H), 7.02-7.05 (m, 1H), 5.75 (s, 1H), 3.61 (s, 3H), 3.54-3.70 (m, 6H), 3.33-3.38 (m, 2H), 1.81 (s, 2H), 1.46-1.56 (m, 5H).

Example 5: Synthesis of Compound 13

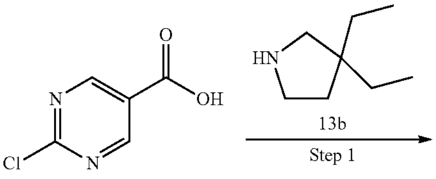

13a

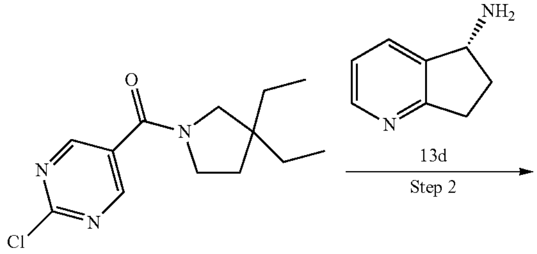

13c

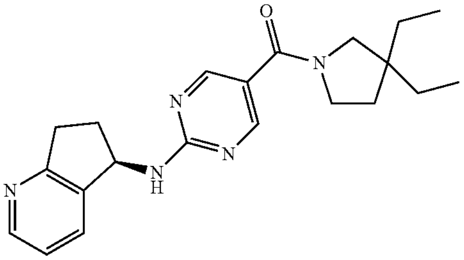

13

Step 1

To a 25 mL three-necked flask was added compound 13a (200 mg, 1.27 mmol), compound 13b (168 mg, 1.33 mmol) and acetonitrile (3 mL), and the reaction mixture was cooled to −10° C., then $T_3P$ (350 mg, 0.4 mol) was slowly added dropwise. The reaction mixture was added with triethylamine (260 mg, 5.54 mmol) dissolved in acetonitrile (5 mL), and the reaction system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 70 mg of white solid as compound 13c with a yield of 20%.

Step 2

To a 10 mL three-necked flask was added successively compound 13c (70 mg, 0.26 mmol), compound 13d (41 mg, 0.28 mol) and isopropanol/water (V/V=99:1, 5 mL), then added potassium carbonate (180 mg, 1.3 mmol). The reaction mixture was heated to 85° C. and stirred at reflux for 4 hours. After the reaction was completed, the reaction mixture was cooled to 45° C., added with acetone (5 mL), and stirred for 1 hour. The mixture was filtered and the filter cake was washed with acetone (5 mL). The filtrate was concentrated to 3 mL, then added with isopropanol (4 mL) and concentrated to 3 mL, then cooled to 0° C. and stirred for 1 hour. The mixture was filtered to obtain 30 mg of off-white solid as compound 13 with a yield of 30%.

LCMS m/z (ESI): 366 [M+1].

$^1$H NMR (400 MHz, DMSO-$d_6$): δ 8.56 (s, 2H), 8.37-8.38 (d, J=2.8 Hz, 1H), 8.11-8.13 (d, J=2.8 Hz, 1H), 7.58-7.59 (m, 1H), 7.13-7.14 (m, 1H), 5.56-5.62 (m, 1H), 3.54-3.65 (m,

2H), 3.49 (s, 1H), 3.27-3.31 (m, 1H), 2.85-3.04 (m, 2H), 2.53-2.55 (s, 1H), 1.98-2.46 (m, 1H), 1.68-1.70 (m, 2H), 1.33-1.42 (m, 4H), 0.76-0.85 (m, 6H).

Example 6: Synthesis of Compound 16

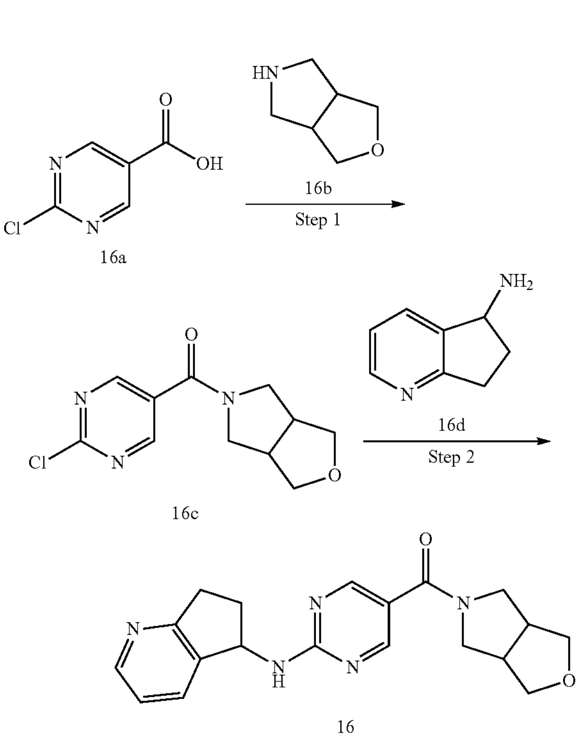

Step 1

To a 25 mL three-necked flask was added compound 16a (150 mg, 0.42 mmol), compound 16b (114 mg, 0.46 mmol) and acetonitrile (2 mL), and the reaction mixture was cooled to −10° C., then $T_3P$ (350 mg, 0.4 mol) was slowly added dropwise. The reaction mixture was added with triethylamine (181 mg, 1.8 mmol) dissolved in acetonitrile (5 mL), and the system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 160 mg of white solid as compound 16c with a yield of 63%.

Step 2

To a 10 mL three-necked flask was added successively compound 16c (160 mg, 0.62 mmol), compound 16d (85 mg, 0.64 mol) and isopropanol/water (v/v=99:1, 10 mL), then added potassium carbonate (0.41 g, 3.2 mmol). The reaction mixture was heated to 85° C. and stirred at reflux for 4 hours. After the reaction was completed, the reaction mixture was cooled to 45° C., added with acetone (5 mL), and stirred for 1 hour. The mixture was filtered and the filter cake was washed with acetone (2 mL). The filtrate was concentrated to 3 mL, then added with isopropanol (4 mL) and concentrated to 3 mL. The mixture was cooled to 0° C. and stirred for 1 hour. The mixture was filtered to obtain 155 mg of off-white solid as compound 16 with a yield of 71%.

LCMS m/z (ESI): 352.1 [M+1].

$^1$H NMR (400 MHz, DMSO-$d_6$) δ 8.59 (s, 2H), 8.37 (d, J=7.54 Hz, 1H), 8.15 (d, J=7.54 Hz, 1H), 7.64-7.56 (m, 1H), 7.17-7.14 (m, 1H), 5.69-5.53 (m, 1H), 3.76-3.63 (m, 4H), 3.55-3.46 (m, 5H), 2.94-2.79 (m, 4H), 2.03-1.97 (m, 1H).

Example 7: Synthesis of Compound 17

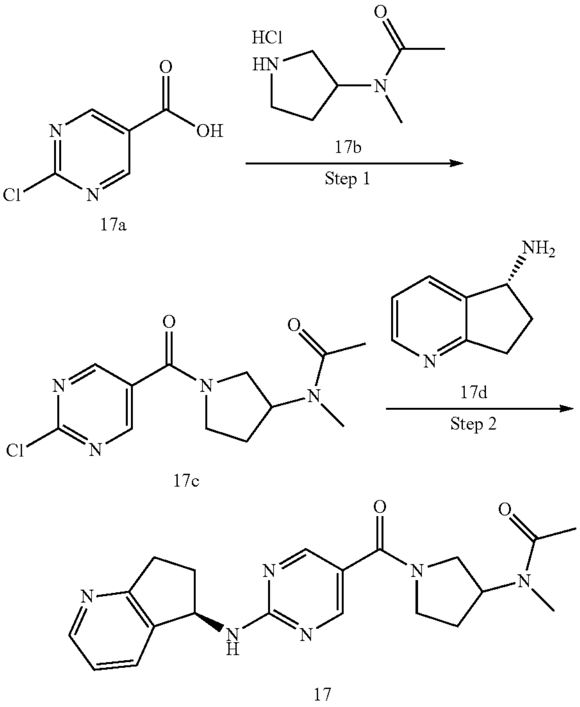

Step 1

To a 25 mL three-necked flask was added compound 17a (150 mg, 0.42 mmol), compound 17b (134 mg, 0.46 mmol) and acetonitrile (2 mL), and the reaction mixture was cooled to −10° C., then $T_3P$ (350 mg, 0.4 mol) was slowly added dropwise. The reaction mixture was added with triethylamine (181 mg, 1.8 mmol) dissolved in acetonitrile (5 mL), and the reaction system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 40 mg of white solid as compound 17c with a yield of 33%.

Step 2

To a 10 mL three-necked flask was added successively compound 17c (40 mg, 0.14 mmol), compound 17d (16 mg, 0.145 mol) and isopropanol/water (v/v=99:1, 3.9 mL), then added potassium carbonate (96.6 mg, 0.7 mmol). The reaction mixture was heated to 85° C. and stirred at reflux for 4 hours. After the reaction was completed, the reaction mixture was extracted with ethyl acetate (10 mL×3). The organic phases were combined and dried over anhydrous sodium sulfate. The mixture was filtered and concentrated to obtain a crude product, which was purified by reversed-phase column chromatography to obtain 25 mg of off-white solid as compound 17 with a yield of 25%.

LCMS m/z (ESI): 381.1 [M+1].

$^1$H NMR (400 MHz, DMSO-$d_6$): δ 8.59 (s, 2H), 8.37 (d, J=7.54 Hz, 1H), 8.15 (d, J=7.54 Hz, 1H), 7.64-7.56 (m, 1H), 7.17-7.14 (m, 1H), 5.69-5.53 (m, 1H), 4.25 (s, 1H), 3.67-3.51 (m, 4H), 3.04-2.91 (m, 4H), 2.86 (s, 1H), 2.58-2.56 (m, 1H), 2.08-1.94 (m, 6H).

Example 8: Synthesis of Compound 19

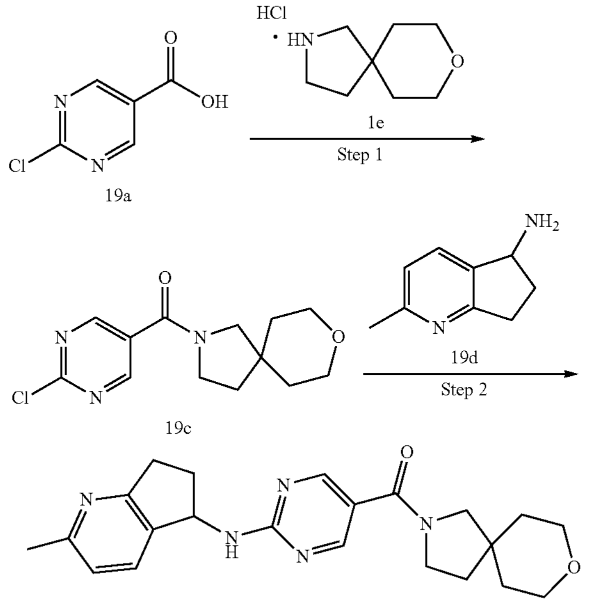

19

Step 1

To a 25 mL three-necked flask was added compound 19a (150 mg, 0.42 mmol), compound 1e (154 mg, 0.46 mmol) and acetonitrile (2 mL), and the reaction mixture was cooled to −10° C., then $T_3P$ (350 mg, 0.4 mol) was slowly added dropwise. The reaction mixture was added with triethylamine (181 mg, 1.8 mmol) dissolved in acetonitrile (5 mL), and the reaction system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 60 mg of white solid as compound 19c with a yield of 33%.

Step 2

To a 10 mL three-necked flask was added successively compound 19c (60 mg, 0.21 mmol), compound 19d (24 mg, 0.22 mol) and isopropanol/water (v/v=99:1, 3.9 mL), then added potassium carbonate (152 mg, 1.1 mmol). The reaction mixture was heated to 85° C. and stirred at reflux for 4 hours. After the reaction was completed, the reaction mixture was extracted with ethyl acetate (10 mL×3). The organic phases were combined and dried over anhydrous sodium sulfate. The mixture was filtered and the filtrate was concentrated to obtain a crude product, which was purified by reversed-phase column chromatography to obtain 16 mg of off-white solid as compound 19 with a yield of 15%.

LCMS m/z (ESI): 394.1 [M+1].

$^1$H NMR (400 MHz, DMSO-$d_6$): δ 8.57 (s, 2H), 8.09 (d, J=7.54 Hz, 1H), 7.49 (d, J=8.0 Hz, 1H), 7.02-7.00 (d, J=8.0 Hz, 1H), 5.60-5.53 (m, 1H), 3.86-3.53 (m, 8H), 2.96-2.85 (m, 2H), 2.43 (s, 3H), 2.00-1.95 (m, 1H), 1.82-1.79 (m, 2H), 1.56-1.47 (m, 5H).

Example 9: Synthesis of Compound 23

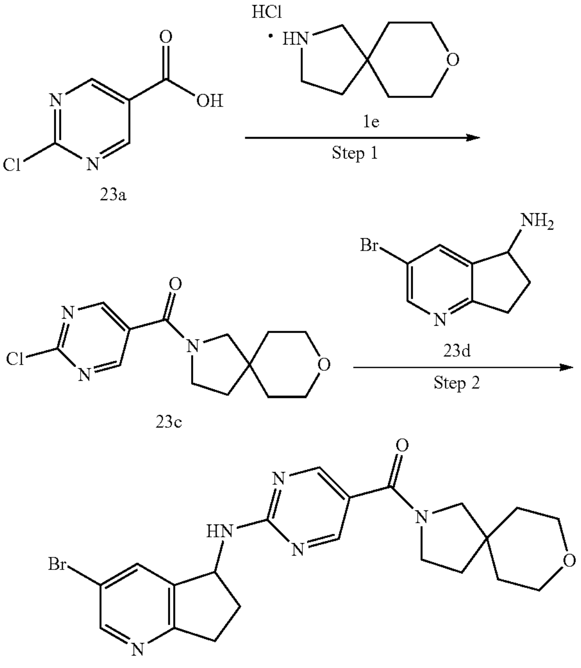

23

Step 1

To a 25 mL three-necked flask was added compound 23a (150 mg, 0.42 mmol), compound 1e (154 mg, 0.46 mmol) and acetonitrile (2 mL), and the reaction mixture was cooled to −10° C., then $T_3P$ (350 mg, 0.4 mol) was slowly added dropwise. The reaction mixture was added with triethylamine (181 mg, 1.8 mmol) dissolved in acetonitrile (5 mL), and the system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 60 mg of white solid as compound 23c with a yield of 33%.

Step 2

To a 10 mL three-necked flask was added successively compound 23c (60 mg, 0.21 mmol), compound 23d (26 mg, 0.22 mol) and isopropanol/water (v/v=99:1, 3.9 mL), then added potassium carbonate (152 mg, 1.1 mmol). The reaction mixture was heated to 85° C. and stirred at reflux for 4 hours. After the reaction was completed, the reaction mixture was cooled to 45° C., added with acetone (5 mL), and stirred for 1 hour. The mixture was filtered and the filter cake was washed with acetone (2 mL). The filtrate was concentrated to 3 mL, then added with isopropanol (4 mL) and concentrated to 3 mL. The mixture was cooled to 0° C. and stirred for 1 hour. The mixture was filtered to obtain 12 mg of off-white solid as compound 23 with a yield of 12%.

LCMS m/z (ESI): 458.1 [M+1].

$^1$H NMR (400 MHz, $CD_3OD$): δ 8.59 (s, 2H), 8.45 (d, J=2.1 Hz, 1H), 7.86-7.84 (m, 1H), 5.70 (t, J=7.9 Hz, 1H), 3.75 (s, 1H), 3.54 (d, J=19.3 Hz, 4H), 3.12-2.88 (m, 4H), 2.73-2.53 (m, 2H), 2.11 (dd, J=13.1, 8.5 Hz, 2H), 1.98-1.90 (m, 4H), 1.66 (d, J=8.4 Hz, 3H).

Example 10: Synthesis of Compound 21

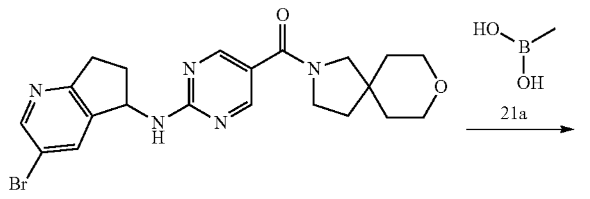

23

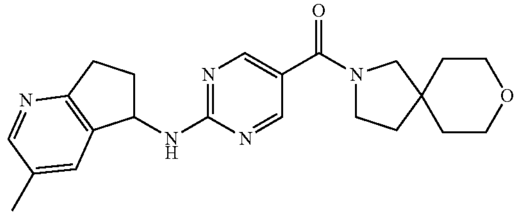

21

Compound 23 (50 mg, 0.10 mmol), methylboronic acid (12 mg, 0.22 mmol), potassium phosphate (60 mg, 0.3 mmol), $Pd(dppf)_2Cl_2$ (16 mg, 0.02 mmol) were added to 2 mL of 1,4-dioxane and 0.5 mL of water, and the reaction mixture was stirred at 100° C. for 3 hours. After the reaction was completed, the reaction mixture was extracted with dichloromethane (10 mL×3). The organic phases were combined, dried and concentrated to obtain 70 mg of a crude product, which was purified by column chromatography (DCM:$CH_3OH$=20:1) to obtain compound 21 (30 mg, yield of 65%).

LCMS m/z (ESI): 394.2 [M+1].

$^1H$ NMR (400 MHz, DMSO-$d_6$) δ 8.57 (s, 2H), 8.22 (s, 1H), 8.10 (d, J=8.4 Hz, 1H), 7.40 (s, 1H), 5.58 (q, J=8.3 Hz, 1H), 3.69-3.45 (m, 7H), 2.89 (dd, J=31.4, 8.2 Hz, 2H), 2.24 (s, 3H), 1.98 (dd, J=12.2, 8.4 Hz, 2H), 1.80 (d, J=7.4 Hz, 2H), 1.51 (d, J=33.8 Hz, 4H).

Example 10: Synthesis of Compound 24

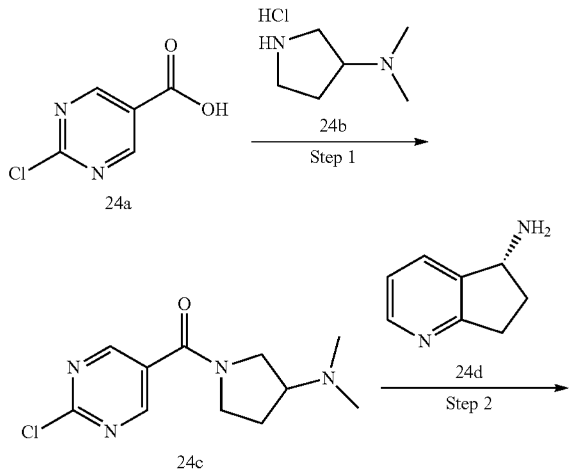

-continued

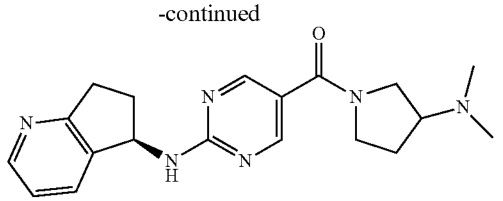

24

Step 1

To a 25 mL three-necked flask was added compound 24a (150 mg, 0.42 mmol), compound 24b (134 mg, 0.46 mmol) and acetonitrile (2 mL), and the reaction mixture was cooled to −10° C., then $T_3P$ (350 mg, 0.4 mol) was slowly added dropwise. The reaction mixture was added triethylamine (181 mg, 1.8 mmol) dissolved in acetonitrile (5 mL), and the system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 20 mg of white solid as compound 24c with a yield of 16%.

Step 2

To a 10 mL three-necked flask was added successively compound 24c (20 mg, 0.14 mmol), compound 24d (8 mg, 0.145 mol) and isopropanol/water (V/V=99:1, 1.9 mL), then added potassium carbonate (0.14 g, 0.98 mmol). The reaction mixture was heated to 85° C. and stirred at reflux for 4 hours. After the reaction was completed, the reaction mixture was extracted with ethyl acetate (10 mL×3). The organic phases were combined and dried over anhydrous sodium sulfate. The mixture was filtered and concentrated to obtain a crude product, which was purified by reversed-phase column chromatography to obtain 8 mg of off-white solid as compound 24 with a yield of 35%.

LCMS m/z (ESI): 353.1 [M+1].

$^1H$ NMR (400 MHz, DMSO-$d_6$): δ 8.56 (s, 1H), 8.38 (d, J=4.8 Hz, 1H), 8.33-8.28 (m, 1H), 7.68 (s, 1H), 7.19-7.14 (m, 1H), 5.60 (d, J=8.1 Hz, 1H), 4.23 (d, J=7.6 Hz, 1H), 3.60 (s, 2H), 2.83 (d, J=26.4 Hz, 4H), 2.36 (ddd, J=15.3, 7.7, 3.6 Hz, 2H), 2.21-2.09 (m, 6H), 2.04-1.97 (m, 2H).

Example 11: Synthesis of Compound 26

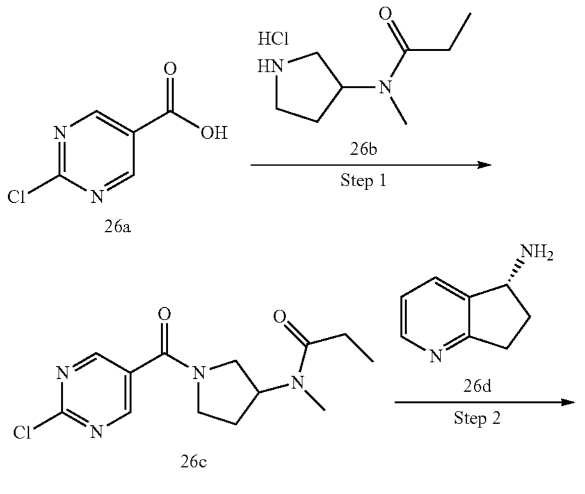

-continued

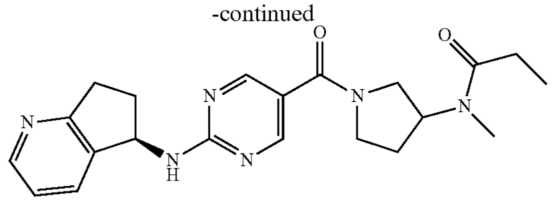

26

Step 1

To a 25 mL three-necked flask was added compound 26a (150 mg, 0.41 mmol), compound 26b (134 mg, 0.45 mmol) and acetonitrile (2 mL), and the reaction mixture was cooled to −10° C., then $T_3P$ (350 mg, 0.4 mol) was slowly added dropwise. The reaction mixture was added with triethylamine (181 mg, 1.8 mmol) dissolved in acetonitrile (5 mL), and the system was kept at −5° C. and stirred for 3 hours. After the reaction was completed, the reaction mixture was added with water (30 mL) to quench. The mixture was concentrated, cooled to 5° C., and stirred for 1 hour. After filtration, the filter cake was washed with water (100 mL) to obtain 40 mg of white solid as compound 26c with a yield of 33%.

Step 2

To a 10 mL three-necked flask was added successively compound 26c (40 mg, 0.14 mmol), compound 26d (16 mg, 0.145 mol) and isopropanol/water (V/V=99:1, 3.9 mL), then added potassium carbonate (99.6 mg, 0.7 mmol). The reaction mixture was heated to 85° C. and stirred at reflux for 4 hours. After the reaction was completed, the reaction mixture was cooled to 45° C., added with acetone (5 mL), and stirred for 1 hour. The mixture was filtered and the filter cake was washed with acetone (2 mL). The filtrate was concentrated to 3 mL, then added with isopropanol (4 mL) and concentrated to 3 mL, then cooled to 0° C. and stirred for 1 hour. The mixture was filtered to obtain 36 mg of gray solid as compound 26 with a yield of 57%.

LCMS: [M+1]=395.1, RT=0.62 min $^1H$ NMR (400 MHz, DMSO-$d_6$) δ ppm 8.55-8.65 (m, 2H), 8.38 (d, J=7.54 Hz, 1H), 8.17 (d, J=7.54 Hz, 1H), 7.71-7.69 (m, 1H), 7.58-7.56 (m, 1H) 5.69-5.53 (m, 1H), 4.25 (s, 1H), 3.76-3.53 (m, 4H), 2.94-2.79 (m, 6H), 2.34-2.24 (m, 2H), 2.03-1.97 (m, 2H), 1.34 (d, J=6.13 Hz, 2H), 1.24 (d, J=5.82 Hz, 3H)

Bioassay Evaluation

1. Vanin-1 Recombinant Enzyme Activity Inhibition Assay

A certain mass of the compound was weighed precisely, and prepared with DMSO and reaction buffer (50 mM Tris base, 50 mM KCl, 1.6 mM cysteamine, 0.005% Brij 35, pH 8.0, prepared when using) to a maximum concentration of 10000 nM, then diluted in a 4-fold gradient, and prepared into 10 compound working solutions with different concentrations;

for the activity inhibition reaction of recombinant human Vanin-1 (Biorab, JN0618), 2.5 μL of compound working solution and 5 μL of recombinant human Vanin-1 protein were first mixed. The mixture was incubated at room temperature for 15 minutes, then added with 2.5 μL of Pantetheine 7-amino-4-trifluoromethylcoumarin substrate, such that the final concentration of recombinant human Vanin-1 was 62.5 μM and the final concentration of Pantetheine 7-amino-4-trifluoromethylcoumarin substrate was 45 μM in the 10 μL reaction system. The reaction was carried out in a 384-well plate (PerkinElmer, 6007280) with DMSO at a final concentration of 1%. The excitation light was set at 405 nm and the emission light was set at 505 nm on the microplate reader, and kinetic reading was performed at 25° C. for 1 hour. Raw data at the 30th minute were collected for data processing and analysis, then the concentration-effect curve was fitted with GraphPad Prism 8 software, and the $IC_{50}$ of the compound concentration was calculated. The data are shown in Table 1 below.

TABLE 1

| Example | $IC_{50}$ (nM) |
|---|---|
| Compound 2 | 8.9 |
| Compound 2-1 | 2.4 |
| Compound 13 | 4.2 |
| Compound 17 | 0.6 |
| Compound 19 | 2.9 |
| Compound 23 | 1.7 |
| Compound 21 | 6.9 |
| Compound 26 | 2.0 |
| Compound A | 11.25 |

Compound A is

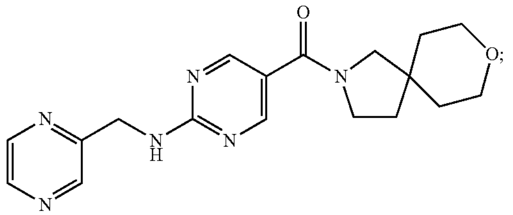 [SMILES: O=C(c1cnc(NCc2cnccn2)nc1)N1CCC2(CCOCC2)C1]

which was prepared with reference to the method of Example 142 in CN109476645A.

2. In Vivo Pharmacokinetic Evaluation in Mice

Experimental Purpose:

To detect pharmacokinetic parameters of the compounds of the present disclosure in C57BL6 mice Experimental Scheme:

The vehicle used in the experiment was: DMSO:Solutol: PBS=5%:25%:70% (v/v/v). Preparation method: The required compound was weighed accurately, added with a certain volume of DMSO in a certain proportion, vortex-mixed until completely dissolved, then added successively with Solutol and PBS according to the above proportion, and mixed well. The vehicles used in the intravenous (iv) administration group and oral (po) administration group were the same vehicles in the experiment. The intravenous dose was 1 mpk and the oral dose was 2 mpk. Experimental blood collection time points: IV group: 0.083, 0.25, 0.5, 1, 2, 4, 7, 24 h. PO group: 200 μL of whole blood was collected from jugular vein at each time point of 0.25, 0.5, 1, 2, 4, 7 and 24 h, anticoagulated with EDTA-K2, and immediately centrifuged at 4000 rpm for 5 minutes at 4° C. The supernatant was taken and the samples were frozen and stored in a refrigerator at −80° C. Processing of plasma samples: The sample was precipitated with ACN/MeOH (1:1, v/v) precipitant containing internal standard, then centrifuged at 14000 rpm for 5 minutes. The supernatant was taken into LC-MS/MS (AB Triple Quard 5500) for analysis to obtain plasma concentrations, and parameters were calculated by the non-compartmental model of Winnolin 8.1 version. The results are shown in Table 2.

TABLE 2

| Compound | Mode of administration | Peak concentration $C_{max}$ (ng/mL) | Half-life $T_{1/2}$ (hr) | Area under the curve $AUC_{0\text{-}7h}$ (hr × ng/mL) | Distributed solvent Vd (L/kg) | Clearance rate CL (mL/hr/kg) | Bio-availability F % |
|---|---|---|---|---|---|---|---|
| Compound 2-1 | Intravenous injection group iv | 722.5 | 2.46 | 406.64 | 8.6 | 2415.50 | — |
| | Intragastric administration group po | 557.4 | 1.56 | 618.38 | 7.5 | 3278.10 | 76.4% |
| Compound 17 | Intravenous injection group iv | 742.33 | 0.93 | 557.60 | 2.60 | 2031.42 | — |
| | Intragastric administration group po | 539.37 | 1.05 | 684.31 | 4.55 | 2919.73 | 61.4% |
| Compound 19 | Intragastric administration group po | 766.60 | 1.52 | 1459.29 | 2.91 | 1316.71 | — |

Note: - means that data cannot be calculated

CONCLUSION

Both compounds 2-1 and 17 exhibited high bioavailability in mice at the given doses, 76.4% and 61.4%, respectively, showing that the compounds of the present disclosure have excellent pharmacokinetic properties.

What is claimed is:

1. A pyrimidine carboxamide compound represented by formula I, or a tautomer, mesomer, racemate, enantiomer, diastereomer thereof, or a mixture form thereof, or a pharmaceutically acceptable salt thereof;

I

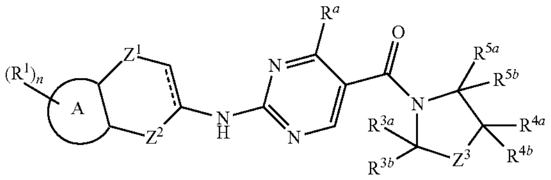

wherein, n is 0, 1, 2 or 3;

$R^1$ is independently halogen, $C_1$-$C_6$ alkyl, $C_1$-$C_6$ alkyl substituted by one or more than one $R^{1a}$;

$Z^1$ is —$(CR^{6a}R^{6b})$— or —$(NR^{6c})$—, and $Z^2$ is a linking bond; or, $Z^1$ is a linking bond, and $Z^2$ is —$(CR^{7a}R^{7b})$—;

$Z^3$ is a linking bond or —$(CR^{8a}R^{8b})$—;

$R^a$ is independently H;

$R^{6a}$, $R^{6b}$, $R^{7a}$ and $R^{7b}$ are independently H, halogen or $C_1$-$C_6$ alkyl;

$R^{6c}$ is independently H or $C_1$-$C_4$ alkyl;

$R^{3a}$, $R^{3b}$, $R^{4a}$, $R^{4b}$, $R^{5a}$, $R^{5b}$, $R^{8a}$ and $R^{8b}$ are independently H, halogen, $C_1$-$C_6$ alkyl, $C_1$-$C_6$ alkyl substituted by one or more than one $R^{1c}$, —$(NR^{9a}R^{9b})$ or —$(NR^{10a})$—(C═O)—$R^{10b}$;

alternatively, $R^{4a}$ and $R^{4b}$, or, $R^{4a}$ and $R^{5a}$, or, $R^{4a}$ and $R^{8a}$ form a ring B together with the carbon to which they are bonded; the ring B is 4- to 7-membered cycloalkyl, 4- to 7-membered heterocycloalkyl, 4- to 7-membered cycloalkyl substituted by one or more than one $R^{1d}$, or 4- to 7-membered heterocycloalkyl substituted by one or more than one $R^{1e}$; the heteroatom of the 4- to 7-membered heterocycloalkyl and the 4- to 7-membered heterocycloalkyl substituted by one or more than one $R^{1e}$ is N, O or S, and the number of heteroatom is 1 or 2;

$R^{1a}$, $R^{1c}$, $R^{1d}$ and $R^{1e}$ are independently halogen, $C_1$-$C_4$ alkyl or $C_1$-$C_4$ alkyl substituted by one or more than one halogen;

$R^{9a}$, $R^{9b}$, $R^{10a}$ and $R^{10b}$ are independently H, $C_1$-$C_4$ alkyl or $C_1$-$C_4$ alkyl substituted by one or more than one halogen;

A is 6-membered heteroaryl; the heteroatom of the 6-membered heteroaryl is N, and the number of heteroatom is 1 or 2;

═ represents a single bond or a double bond.

2. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, n is 0 or 1;

or, $Z^1$ is —$(CR^{6a}R^{6b})$—, and $Z^2$ is the linking bond;

or, $Z^3$ is —$(CR^{8a}R^{8b})$—;

or, $R^{6a}$ and $R^{6b}$ are independently H or halogen;

or, $R^{7a}$ and $R^{7b}$ are independently H;

or, $R^{3a}$ and $R^{3b}$ are independently H;

or, $R^{4a}$ and $R^{4b}$ are independently H, $C_1$-$C_6$ alkyl, —$(NR^{9a}R^{9b})$ or —$(NR^{10a})$—(C═O)—$R^{10b}$;

or, $R^{5a}$ and $R^{5b}$ are independently H;

or, ring B is 4- to 7-membered cycloalkyl, 4- to 7-membered heterocycloalkyl, 4- to 7-membered heterocycloalkyl substituted by one or more than one $R^{1e}$, or, $R^{8a}$ and $R^{8b}$ are independently H;

or, $R^{1a}$, $R^{1c}$, $R^{1d}$ and $R^{1e}$ are independently halogen or $C_1$-$C_4$ alkyl;

or, $R^{9a}$, $R^{9b}$, $R^{10a}$ and $R^{10b}$ are independently $C_1$-$C_4$ alkyl or $C_1$-$C_4$ alkyl substituted by one or more than one halogen;

or, ═ represents the single bond;

or,

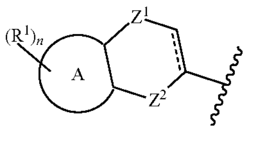

is

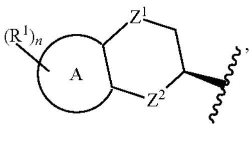

,

-continued

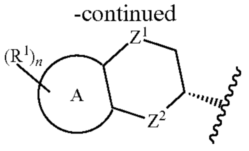

or a mixture thereof.

3. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, the compound is adapted to scheme 1 or scheme 2;

scheme 1:

n is 0 or 1;

$R^1$ is independently halogen, $C_1$-$C_6$ alkyl, $C_1$-$C_6$ alkyl substituted by one or more than one $R^{1a}$;

$Z^1$ is —$(CR^{6a}R^{6b})$— or —$(NR^{6c})$—, and $Z^2$ is the linking bond; or, $Z^1$ is the linking bond, and $Z^2$ is —$(CR^{7a}R^{7b})$—;

$Z^3$ is —$(CR^{8a}R^{8b})$—;

$R^a$ is independently H;

$R^{6a}$, $R^{6b}$, $R^{7a}$ and $R^{7b}$ are independently H or halogen;

$R^{6c}$ is independently H or $C_1$-$C_4$ alkyl;

$R^{3a}$, $R^{3b}$, $R^{5a}$, $R^{5b}$, $R^{8a}$ and $R^{8b}$ are independently H;

$R^{4a}$ and $R^{4b}$ are independently H, $C_1$-$C_6$ alkyl, —$(NR^{9a}R^{9b})$ or —$(NR^{10a})$—(C═O)—$R^{10b}$;

alternatively, $R^{4a}$ and $R^{4b}$, or, $R^{4a}$ and $R^{5a}$, or, $R^{4a}$ and $R^{8a}$ form the ring B together with the carbon to which they are bonded; the ring B is 4- to 7-membered cycloalkyl, 4- to 7-membered heterocycloalkyl, 4- to 7-membered cycloalkyl substituted by one or more than one $R^{1d}$, or 4- to 7-membered heterocycloalkyl substituted by one or more than one $R^{1e}$, $R^{1a}$, $R^{1d}$ and $R^{1e}$ are independently halogen or $C_1$-$C_4$ alkyl;

$R^{9a}$, $R^{9b}$, $R^{10a}$ and $R^{10b}$ are independently $C_1$-$C_4$ alkyl or $C_1$-$C_4$ alkyl substituted by one or more than one halogen;

A is 6-membered heteroaryl;

scheme 2:

n is 0 or 1;

$R^1$ is independently halogen, $C_1$-$C_6$ alkyl, $C_1$-$C_6$ alkyl substituted by one or more than one $R^{1a}$, $Z^1$ is —$(CR^{6a}R^{6b})$— or —$(NR^{6c})$—, and $Z^2$ is the linking bond; or, $Z^1$ is the linking bond, and $Z^2$ is —$(CR^{7a}R^{7b})$—;

$Z^3$ is —$(CR^{8a}R^{8b})$—;

$R^a$ is independently H;

$R^{6a}$ and Rób are independently H or halogen; $R^{7a}$ and $R^{7b}$ are independently H;

$R^{1a}$ is independently halogen;

$R^{1c}$ is independently H or $C_1$-$C_4$ alkyl;

$R^{3a}$, $R^{3b}$, $R^{5a}$, $R^{5b}$, $R^{8a}$ and $R^{8b}$ are independently H;

$R^{4a}$ is independently $C_1$-$C_6$ alkyl, —$(NR^{9a}R^{9b})$ or —$(NR^{10a})$—(C═O)—$R^{10b}$;

$R^{4b}$ is independently H or $C_1$-$C_6$ alkyl;

alternatively, $R^{4a}$ and $R^{4b}$, or, $R^{4a}$ and $R^{5a}$, or, $R^{4a}$ and $R^{8a}$ form the ring B together with the carbon to which they are bonded; the ring B is 4- to 7-membered cycloalkyl, 4- to 7-membered heterocycloalkyl, or 4- to 7-membered heterocycloalkyl substituted by one or more than one $R^{1e}$, $R^{1e}$ is independently $C_1$-$C_4$ alkyl;

$R^{9a}$, $R^{9b}$, $R^{10a}$ and $R^{10b}$ are independently $C_1$-$C_4$ alkyl or $C_1$-$C_4$ alkyl substituted by one or more than one halogen;

A is 6-membered heteroaryl;

⎓ represents the single bond.

4. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, when $R^1$ is halogen, the halogen is fluorine, chlorine or bromine;

or, when $R^1$ is $C_1$-$C_6$ alkyl substituted by one or more than one $R^{1a}$, the number of the substituent is 1, 2, 3, 4 or 5;

or, when $R^1$ is $C_1$-$C_6$ alkyl or $C_1$-$C_6$ alkyl substituted by one or more than one $R^{1a}$, the $C_1$-$C_6$ alkyl is independently methyl, ethyl, n-propyl, isopropyl, n-butyl, isobutyl, sec-butyl or tert-butyl;

or, when $R^{6a}$, $R^{6b}$, $R^{7a}$ and $R^{7b}$ are independently halogen, the halogen is independently fluorine, chlorine or bromine;

or, when $R^{6a}$, $R^{6b}$, $R^{7a}$ and $R^{7b}$ are independently $C_1$-$C_6$ alkyl, the $C_1$-$C_6$ alkyl is independently methyl, ethyl, n-propyl, isopropyl, n-butyl, isobutyl, sec-butyl or tert-butyl;

or, when $R^{6c}$ is independently $C_1$-$C_4$ alkyl, the $C_1$-$C_4$ alkyl is independently methyl, ethyl, n-propyl, isopropyl, n-butyl, isobutyl, sec-butyl or tert-butyl;

or, when $R^{3a}$, $R^{3b}$, $R^{4a}$, $R^{4b}$, $R^{5a}$, $R^{5b}$, $R^{8a}$ and $R^{8b}$ are independently halogen, the halogen is independently fluorine, chlorine or bromine;

or, when $R^{3a}$, $R^{3b}$, $R^{4a}$, $R^{4b}$, $R^{5a}$, $R^{5b}$, $R^{8a}$ and $R^{8b}$ are independently $C_1$-$C_6$ alkyl or $C_1$-$C_6$ alkyl substituted by one or more than one $R^{1c}$, the $C_1$-$C_6$ alkyl is independently methyl, ethyl, n-propyl, isopropyl, n-butyl, isobutyl, sec-butyl or tert-butyl;

or, when the ring B is 4- to 7-membered cycloalkyl or 4- to 7-membered cycloalkyl substituted by one or more than one $R^{1d}$, the 4- to 7-membered cycloalkyl is independently cyclobutyl, cyclopentyl, cyclohexyl or cycloheptyl;

or, when the ring B is 4- to 7-membered heterocycloalkyl or 4- to 7-membered heterocycloalkyl substituted by one or more than one $R^{1e}$, the 4- to 7-membered heterocycloalkyl is independently tetrahydrofuranyl, tetrahydro-2H-pyranyl, pyrrolidinyl;

or, when $R^{1a}$, $R^{1c}$, $R^{1d}$ and $R^{1e}$ are independently halogen or $C_1$-$C_4$ alkyl substituted by one or more than one halogen, the halogen is independently fluorine, chlorine or bromine;

or, when $R^{1a}$, $R^{1c}$, $R^{1d}$ and $R^{1e}$ are independently $C_1$-$C_4$ alkyl or $C_1$-$C_4$ alkyl substituted by one or more than one halogen, the $C_1$-$C_4$ alkyl is independently methyl, ethyl, n-propyl, isopropyl, n-butyl, isobutyl, sec-butyl or tert-butyl;

or, when $R^{9a}$, $R^{9b}$, $R^{10a}$ and $R^{10b}$ are independently $C_1$-$C_4$ alkyl, the $C_1$-$C_4$ alkyl is independently methyl, ethyl, n-propyl, isopropyl, n-butyl, isobutyl, sec-butyl or tert-butyl;

or, when $R^{9a}$, $R^{9b}$, $R^{10a}$ and $R^{10b}$ are independently $C_1$-$C_4$ alkyl substituted by one or more than one halogen, the $C_1$-$C_4$ alkyl is independently methyl, ethyl, n-propyl, isopropyl, n-butyl, isobutyl, sec-butyl or tert-butyl;

or, when $R^{9a}$, $R^{9b}$, $R^{10a}$ and $R^{10b}$ are independently $C_1$-$C_4$ alkyl substituted by one or more than one halogen, the halogen is independently fluorine, chlorine or bromine;

or, when A is 6-membered heteroaryl, the 6-membered heteroaryl is pyridyl, pyrazinyl or pyrimidinyl.

5. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, $R^1$ is independently F, methyl or trifluoromethyl;

or, $Z^1$ is the linking bond, —$(CH_2)$—, —$(CF_2)$—, —(NH)— or —$(N(CH_3))$—;

or, $R^{4a}$ and $R^{4b}$ are independently H, ethyl, dimethylamino,

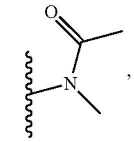
,
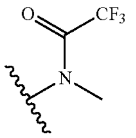
or
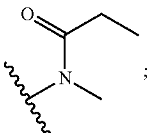
;

or, the ring B is

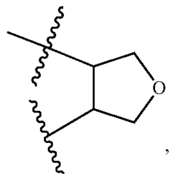
,
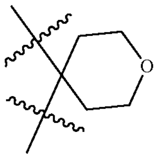
,
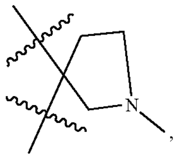
,
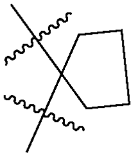
,
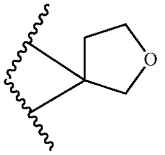
or
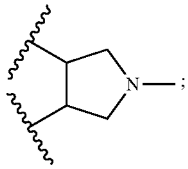
; or,
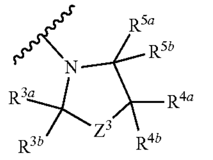
is
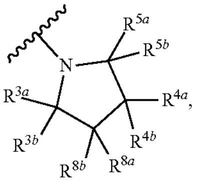
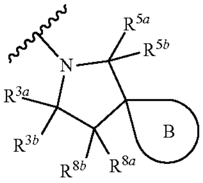
or
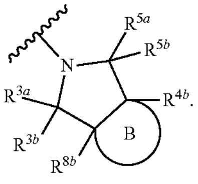
.

6. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, the pyrimidine carboxamide compound represented by formula I is any one of the following structures:

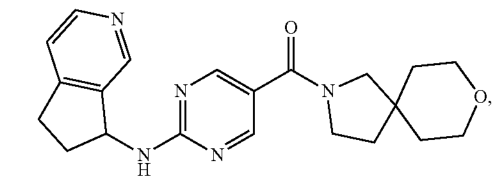
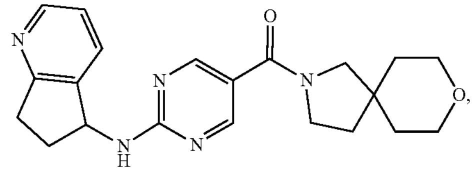
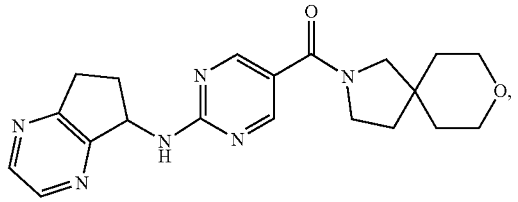
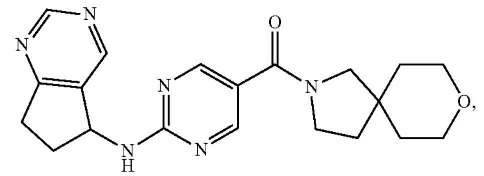
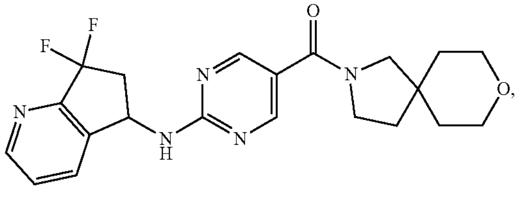
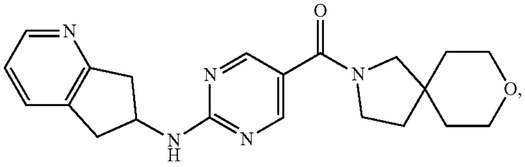
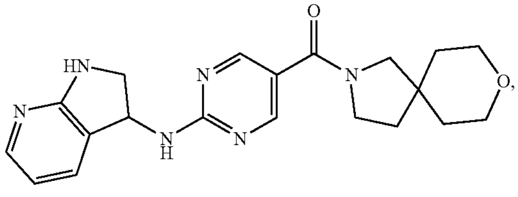
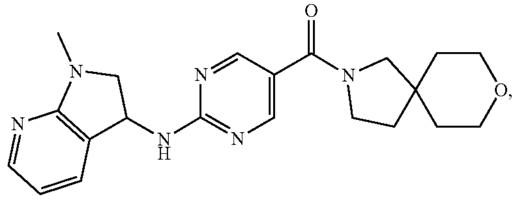
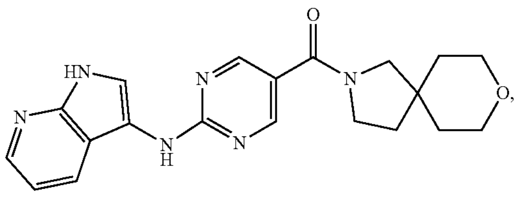

-continued
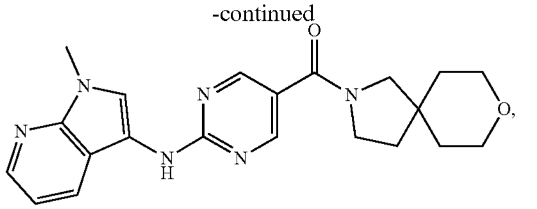
,
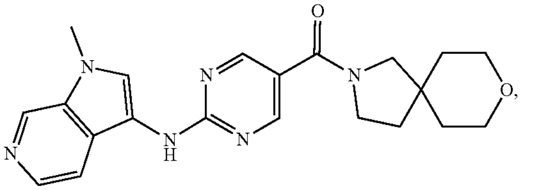
,
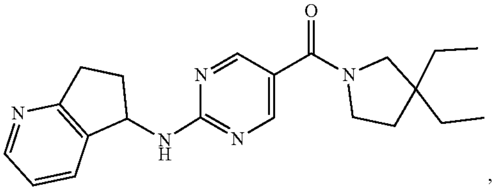
,
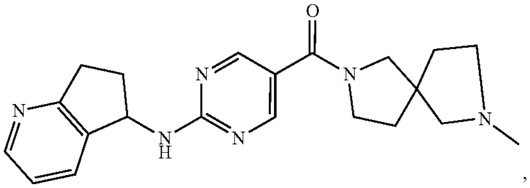
,
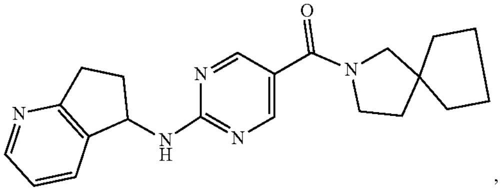
,
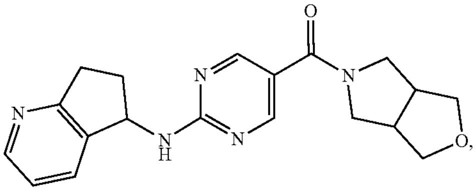
,
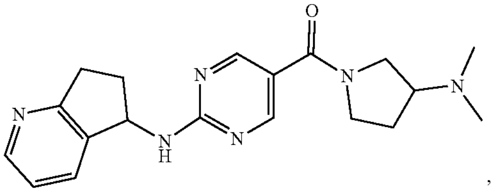
,
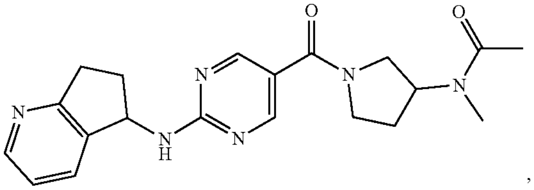
,
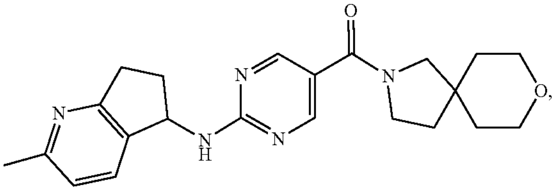
,
-continued
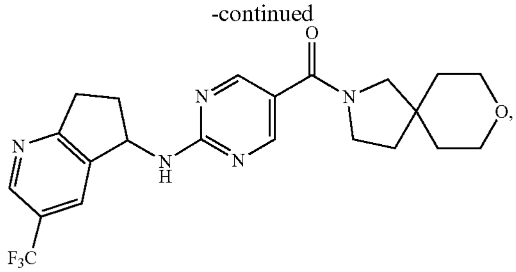
,
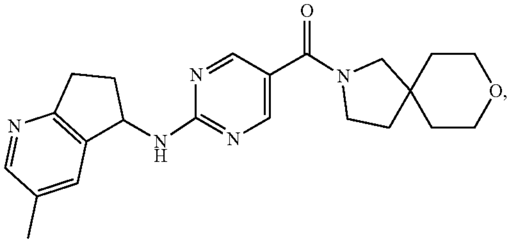
,
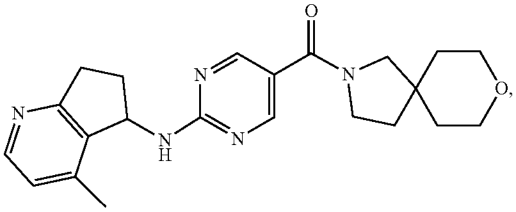
,
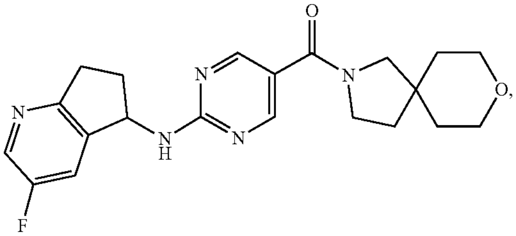
,
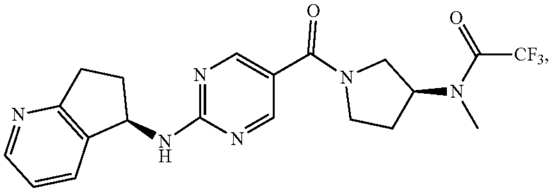
,
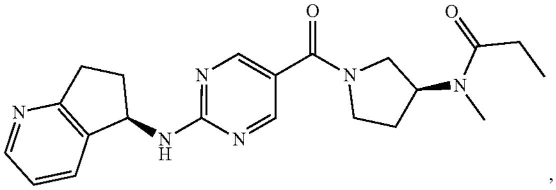
,
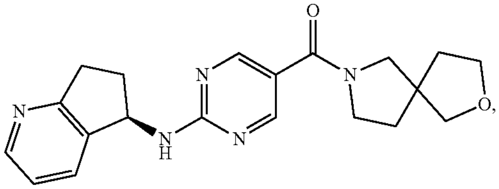
,
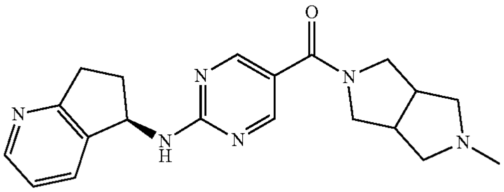
, -continued

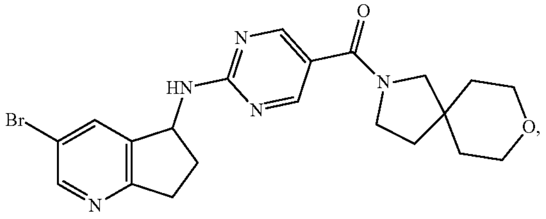

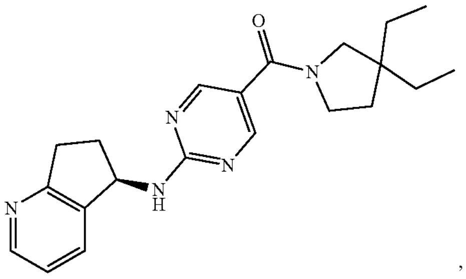

,

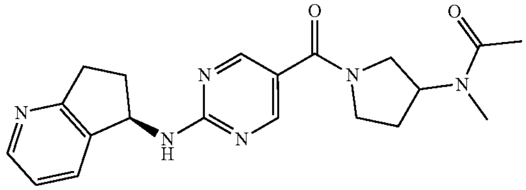

,

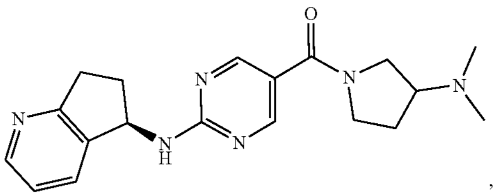

,

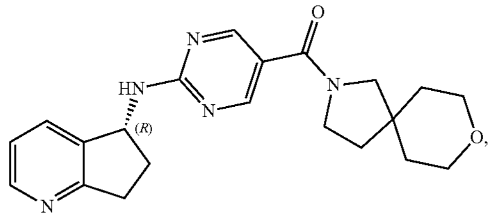

or

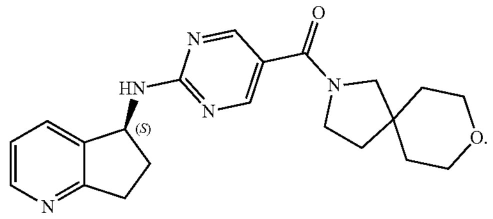

7. The pyrimidine carboxamide compound represented by formula I, or the tautomer, mesomer, racemate, enantiomer, diastereomer thereof, or the mixture form thereof, or the pharmaceutically acceptable salt thereof according to claim 1, wherein, the pyrimidine carboxamide compound represented by formula I is any one of the following structures:

compound

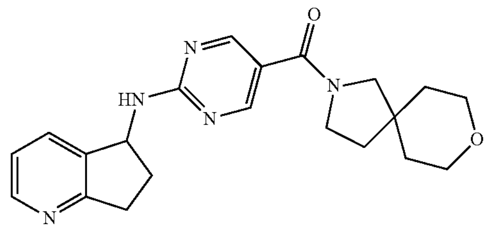 [SMILES: O=C(c1cnc(NC2CCc3ncccc32)nc1)N1CCC2(CCOCC2)C1]

with a retention time of 8.483 min under the following conditions: chiral chromatographic resolution, chromatographic column: 250×4.6 mm, 5 μm; column temperature: 35° C.; flow rate: 0.4 mL/min; wavelength: 254 nm; gradient: A: n-hexane, B: isopropanol, A: B=1:4; run time: 50 min;

compound

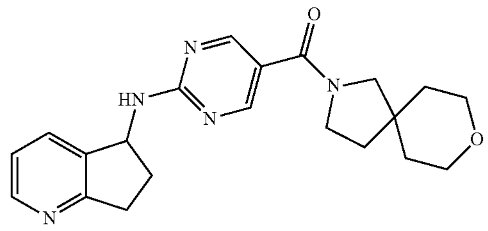 [SMILES: O=C(c1cnc(NC2CCc3ncccc32)nc1)N1CCC2(CCOCC2)C1]

with a retention time of 13.580 min under the following conditions: chiral chromatographic resolution, chromatographic column: 250×4.6 mm, 5 μm; column temperature: 35° C.; flow rate: 0.4 mL/min; wavelength: 254 nm; gradient: A: n-hexane, B: isopropanol, A: B=1:4; run time: 50 min.

8. A pharmaceutical composition, comprising the pyrimidine carboxamide compound represented by formula I, or the tautomer, mesomer, racemate, enantiomer, diastereomer thereof, or the mixture form thereof, or the pharmaceutically acceptable salt thereof according to claim 1, and a pharmaceutical excipient.

9. A method for inhibiting Vanin-1 in a subject in need thereof, comprising: administering the pyrimidine carboxamide compound represented by formula I, or the tautomer, mesomer, racemate, enantiomer, diastereomer thereof, or the mixture form thereof, or the pharmaceutically acceptable salt thereof according to claim 1 to the subject.

10. A method for preventing and/or treating diseases related to Vanin-1 in a subject in need thereof, comprising: administering the pyrimidine carboxamide compound represented by formula I, or the tautomer, mesomer, racemate, enantiomer, diastereomer thereof, or the mixture form thereof, or the pharmaceutically acceptable salt thereof according to claim 1 to the subject.

11. The pyrimidine carboxamide compound represented by formula I, or the tautomer, mesomer, racemate, enantiomer, diastereomer thereof, or the mixture form thereof, or the pharmaceutically acceptable salt thereof according to claim 4, wherein, when $R^1$ is halogen, the halogen is fluorine or chlorine; or, when $R^1$ is $C_1$-$C_6$ alkyl substituted by one or more than one $R^{1a}$, the number of the substituent is 1, 2 or 3;

or, when $R^1$ is $C_1$-$C_6$ alkyl or $C_1$-$C_6$ alkyl substituted by one or more than one $R^{1a}$, the $C_1$-$C_6$ alkyl is independently methyl;

or, when $R^{6a}$, $R^{6b}$, $R^{7a}$ and $R^{7b}$ are independently halogen, the halogen is independently fluorine or chlorine;

or, when $R^{6a}$, $R^{6b}$, $R^{7a}$ and $R^{7b}$ are independently $C_1$-$C_6$ alkyl, the $C_1$-$C_6$ alkyl is independently methyl;

or, when $R^{6c}$ is independently $C_1$-$C_4$ alkyl, the $C_1$-$C_4$ alkyl is independently methyl;

or, when $R^{3a}$, $R^{3b}$, $R^{4a}$, $R^{4b}$, $R^{5a}$, $R^{5b}$, $R^{8a}$ and $R^{8b}$ are independently halogen, the halogen is independently fluorine or chlorine;

or, when $R^{3a}$, $R^{3b}$, $R^{4a}$, $R^{4b}$, $R^{5a}$, $R^{5b}$, $R^{8a}$ and $R^{8b}$ are independently $C_1$-$C_6$ alkyl or $C_1$-$C_6$ alkyl substituted by one or more than one $R^{1c}$, the $C_1$-$C_6$ alkyl is independently methyl or ethyl;

or, when the ring B is 4- to 7-membered cycloalkyl or 4- to 7-membered cycloalkyl substituted by one or more than one $R^{1d}$, the 4- to 7-membered cycloalkyl is independently cyclopentyl;

or, when $R^{4a}$ and $R^{4b}$ form the ring B together with the carbon to which they are bonded, the ring B is

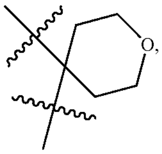, 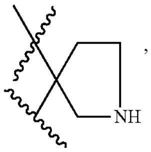, 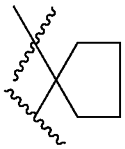 or

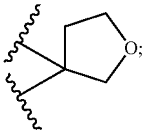;

when $R^{4a}$ and $R^{5a}$, or, $R^{4a}$ and $R^{8a}$ form the ring B together with the carbon to which they are bonded, the ring B is

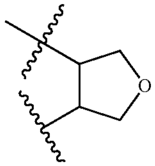 or 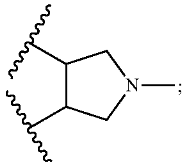;

or, when $R^{1a}$, $R^{1c}$, $R^{1d}$ and $R^{1e}$ are independently halogen or $C_1$-$C_4$ alkyl substituted by one or more than one halogen, the halogen is independently fluorine or chlorine;

or, when $R^{1a}$, $R^{1c}$, $R^{1d}$ and $R^{1e}$ are independently $C_1$-$C_4$ alkyl or $C_1$-$C_4$ alkyl substituted by one or more than one halogen, the $C_1$-$C_4$ alkyl is independently methyl or ethyl;

or, when $R^{9a}$, $R^{9b}$, $R^{10a}$ and $R^{10b}$ are independently $C_1$-$C_4$ alkyl, the $C_1$-$C_4$ alkyl is independently methyl or ethyl;

or, when $R^{9a}$, $R^{9b}$, $R^{10a}$ and $R^{10b}$ are independently $C_1$-$C_4$ alkyl substituted by one or more than one halogen, the $C_1$-$C_4$ alkyl is independently methyl or ethyl;

or, when $R^{9a}$, $R^{9b}$, $R^{10a}$ and $R^{10b}$ are independently $C_1$-$C_4$ alkyl substituted by one or more than one halogen, the halogen is independently fluorine;

or, when A is 6-membered heteroaryl, the 6-membered heteroaryl is pyridyl, pyrazinyl or pyrimidinyl; the pyridyl is

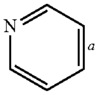 or 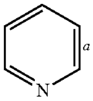, or the pyrazinyl is

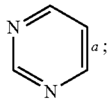;

or the pyrimidinyl is

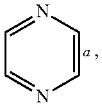, a represents a common bond between A and

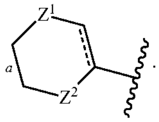.

12. The pyrimidine carboxamide compound represented by formula I, or the tautomer, mesomer, racemate, enantiomer, diastereomer thereof, or the mixture form thereof, or the pharmaceutically acceptable salt thereof according to claim 11, wherein, when $R^1$ is halogen, the halogen is fluorine;

or, when $R^{9a}$, $R^{9b}$, $R^{10a}$ and $R^{10b}$ are independently $C_1$-$C_4$ alkyl substituted by one or more than one halogen, the $C_1$-$C_4$ alkyl substituted by one or more than one halogen is trifluoromethyl.

13. The pyrimidine carboxamide compound represented by formula I, or the tautomer, mesomer, racemate, enantiomer, diastereomer thereof, or the mixture form thereof, or the pharmaceutically acceptable salt thereof according to claim 5, wherein,

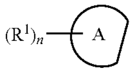

is

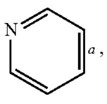, 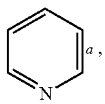, 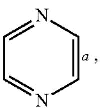, 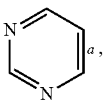,

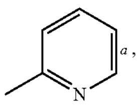, 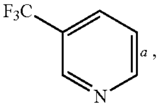, 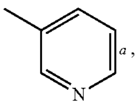,

-continued

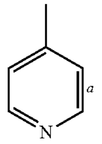

or

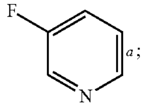

a represents the position of fusion;

or

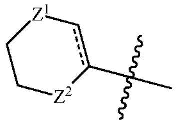

is

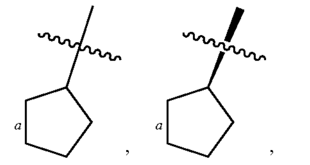

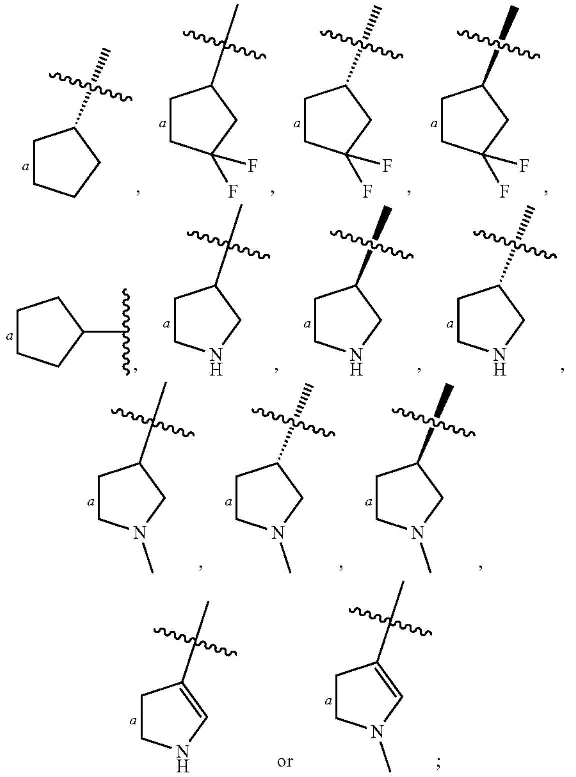

or a represents the position of fusion;

or,

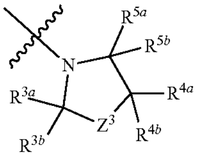

is

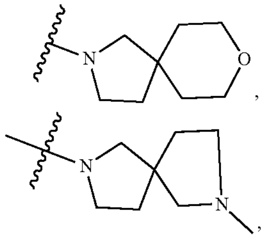

-continued

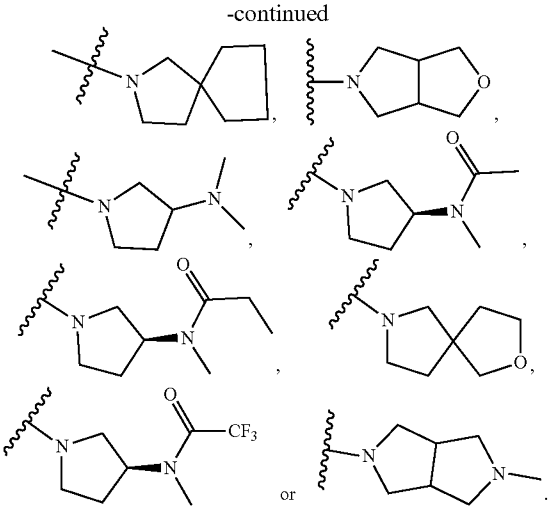

or

14. A method for inhibiting Vanin-1 in a subject in need thereof, comprising: administering the pyrimidine carboxamide compound represented by formula I, or the tautomer, mesomer, racemate, enantiomer, diastereomer thereof, or the mixture form thereof, or the pharmaceutically acceptable salt thereof according to claim 6 to the subject.

15. The method according to claim 10, wherein, the diseases related to Vanin-1 are one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases.

16. The method according to claim 15, wherein one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases are selected from Crohn's disease, ulcerative colitis, inflammatory bowel disease and gastritis.

17. A method for preventing and/or treating diseases related to Vanin-1 in a subject in need thereof, comprising: administering the pyrimidine carboxamide compound represented by formula I, or the tautomer, mesomer, racemate, enantiomer, diastereomer thereof, or the mixture form thereof, or the pharmaceutically acceptable salt thereof according to claim 6 to the subject.

18. The method according to claim 17, wherein, the diseases related to Vanin-1 are one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases.

19. The method according to claim 18, wherein one or more of autoimmune diseases, inflammatory diseases, allergic diseases, metabolic diseases, infection-based diseases, fibrotic diseases, cardiovascular diseases, respiratory diseases, renal diseases, dermatological diseases, liver diseases, gastrointestinal diseases, oral diseases and hematopoietic diseases are selected from Crohn's disease, ulcerative colitis, inflammatory bowel disease and gastritis.

* * * * *